United States Patent [19]

Duffin

[11] Patent Number: 5,193,550
[45] Date of Patent: Mar. 16, 1993

[54] METHOD AND APPARATUS FOR DISCRIMINATING AMONG NORMAL AND PATHOLOGICAL TACHYARRHYTHMIAS

[75] Inventor: Edwin G. Duffin, New Brighton, Minn.

[73] Assignee: Medtronic, Inc., Minneapolis, Minn.

[21] Appl. No.: 621,133

[22] Filed: Nov. 30, 1990

[51] Int. Cl.⁵ .......................................... A61B 5/0464
[52] U.S. Cl. .................................. 128/697; 128/705; 128/702
[58] Field of Search ................. 128/705, 702, 696, 697

[56] References Cited

U.S. PATENT DOCUMENTS

| Re. 27,757 | 3/1987 | Mirowski | 128/419 D |
|---|---|---|---|
| 4,059,116 | 11/1977 | Adams | 128/419 PG |
| 4,384,585 | 5/1983 | Zipes | 128/419 D |
| 4,523,595 | 6/1985 | Zibell | 128/419 D |
| 4,802,483 | 2/1989 | Lindgren | 128/419 PG |
| 4,860,749 | 8/1989 | Lehmann | 128/419 PG |

FOREIGN PATENT DOCUMENTS

| 0202748 | 11/1986 | European Pat. Off. |
| 0308536 | 3/1989 | European Pat. Off. |
| 2524808 | 10/1983 | France |

OTHER PUBLICATIONS

"Necessity of Signal Processing in Tachycardia Detection" by Seymour Furman et al., Future Publications, 1982, pp. 265-274.
"Automatic Tachycardia Recognition" by R. Arzbaecher et al. (PACE, May-Jun. 1984, pp. 541-547).
"Automatic Implantable Cardioverter Defibrillator Structural Characteristics" by Mower et al. PACE, vol. 7, Nov.-Dec., 1984, Part II, pp. 1331-1334.
"Experimental Ventricular Defibrillation with an Automatic and Completely Implanted System", by Schuder et al., Transaction Society for Artificial Internal Organs, 16:207, 1970.

*Primary Examiner*—Kyle L. Howell
*Assistant Examiner*—Scott M. Getzow
*Attorney, Agent, or Firm*—Reed A. Duthler; Harold R. Patton

[57] ABSTRACT

A method and apparatus for discriminating among the various normal and pathologic tachycardias. In response to the detection of tachycardia, far-field ventricular electrograms sensed using atrial electrodes and far-field atrial electrograms sensed using ventricular electrodes are analyzed in order to categorize the source and type of tachyarrhythmia detected. The detection method and apparatus may be employed in conjunction with dual chamber anti-bradycardia pacemakers to avoid pacemaker mediated tachycardias or may be employed to mediate the delivery of pacing energy or cardioversion/defibrillation shock energy to a malfunctioning heart, in the context of an implantable antitachycardia device.

42 Claims, 14 Drawing Sheets

FIG. 3A BIPOLAR ATRIAL EGM
NEAR-FIELD ATRIAL EGM

FIG. 3B HIGH GAIN
UNIPOLAR VENTRICULAR EGM
FAR-FIELD ATRIAL EGM

FIG. 3C BIPOLAR VENTRICULAR EGM
NEAR-FIELD VENTRICULAR EGM

FIG. 3D HIGH GAIN
UNIPOLAR ATRIAL EGM
FAR-FIELD VENTRICULAR EGM $$\begin{cases} (1) \quad y = a_1 x + a_0 \quad\quad (2) \quad \bar{y} = \frac{\Sigma y}{n} \quad\quad (3) \quad \bar{x} = \frac{\Sigma x}{n} \\\\ (4) \quad a_0 = \bar{y} - a_1 \bar{x} \quad\quad (5) \quad a_1 = \frac{n\Sigma xy - \Sigma x \Sigma y}{n\Sigma x^2 - (\Sigma x)^2} \\\\ (6) \quad r^2 = \frac{[n\Sigma xy - \Sigma x \Sigma y]^2}{[n\Sigma x^2 - (\Sigma x)^2][n\Sigma y^2 - (\Sigma y)^2]} \end{cases}$$

FIG. 10

METHOD AND APPARATUS FOR DISCRIMINATING AMONG NORMAL AND PATHOLOGICAL TACHYARRHYTHMIAS

BACKGROUND OF THE INVENTION

1. Field of the Invention

This invention relates generally to implanted medical devices and, more particularly, relates to a physiological waveform morphology discrimination method and apparatus for use in characterizing the origin of cardiac depolarizations and adjusting the operation of the medical device accordingly.

2. Description of Prior Art

Early automatic tachycardia detection systems for automatic implantable cardioverter/defibrillators relied upon the presence or absence of electrical and mechanical heart activity (such as intramyocardial pressure, blood pressure, impedance, stroke volume or heart movement) and/or the rate of the electrocardiogram. For example, the 1961 pamphlet by Dr. Fred Zacouto, Paris, France, entitled. "Traitement D'Urgence des Differents Type de Syncopes Cardiaques du Syndrome de Morgangni-Adams Stokes" (National Library of Medicine) describes an automatic pacemaker and defibrillator responsive to the presence or absence of the patient's blood pressure in conjunction with the rate of the patient's electrocardiogram. Later detection algorithms proposed by Satinsky, "Heart Monitor Automatically Activates Defibrillator," Medical Tribune, 9, No. 9I:3, Nov. 11, 1968, and Schuder et al "Experimental Ventricular Defibrillation with an Automatic and Completely Implanted System," Transactions American Society for Artificial Internal Organs, 16:207, 1970, automatically detected and triggered defibrillation when the amplitude of the R-wave of the electrocardiogram fell below a predetermined threshold over a predetermined period of time. The initial system proposed by Mirowski et al in U.S. Pat. No. Re. 27,757, which similarly relied upon the decrease in the amplitude of a pulsatile right ventricular pressure signal below a threshold over a predetermined period of time, was abandoned by Mirowski et al in favor of the rate and/or probability density function morphology discrimination as described in Mower et al, "Automatic Implantable Cardioverter Defibrillator Structural Characteristics," PACE, Vol. 7, November December 1984, Part 11, pp. 1331-1334. Others have suggested the use of high rate plus acceleration of rate or "onset" (U.S. Pat. No. 4,384,585) with sustained high rate and rate stability (U.S. Pat. No. 4,523,595).

Very generally, the systems that depend upon the aforementioned criteria are capable of discriminating tachyarrhythmia in greater or lesser degree from normal heart rhythm but have difficulty discriminating sinus or other supraventricular tachycardias from malignant, pathologic ventricular tachycardias, resulting in the delivery of inappropriate cardiac electrical stimulation therapies.

A stated in the article "Automatic Tachycardia Recognition" by R. Arzbaecher et al (PACE, May-June 1984, pp. 541-547), antitachycardia pacemakers that were undergoing clinical studies prior to the publication of that article detected tachycardia by sensing a high rate in the chamber to be paced. The specific criteria to be met before pace termination was to be attempted involved a comparison of the detected rate to a preset threshold, such as 150 beats per minute (400 millisecond cycle length) for a pre-selected number of beats. As stated above, other researchers had suggested the rate of change of rate or suddenness of onset, rate stability and sustained high rate a additional criteria to distinguish sinus tachycardias from malignant tachycardias. Arzbaecher et al proposed in their article an algorithm implemented in a microprocessor based implantable device employing both atrial and ventricular rate detection via separate bipolar leads in order to detect the AA and VA, or VV and AV intervals (or "cycle lengths") against threshold intervals in order to distinguish pace-terminable and nonpace-terminable tachycardias. Arzbaecher et al introduced the concept of employing a single atrial extra stimulus to distinguish sinus tachycardia from 1:1 paroxysmal tachycardia in order to determine whether a ventricular response would be elicited. An atrial extra stimulus was delivered in late diastole (80 milliseconds premature), and the ventricular response, if appearing early as well, indicated that the patient was in sinus rhythm. However, in pace-terminable tachycardias, such as AV reentrant and ventricular with VA conduction tachycardia, the ventricular response would not occur early (indicating that the atrial and ventricular rhythms were disassociated) and the ventricular rhythm would be unperturbed.

Other proposals for employing atrial and ventricular detection and interval comparison are set forth in *The Third Decade of Cardiac Pacing: Advances in Technology in Clinical Applications,* Part III, Chapter 1, "Necessity of Signal Processing in Tachycardia Detection" by Furman et al (edited by S. Barold and J. Mugica, Future Publications, 1982, pages 265-274) and in the Lehmann U.S. Pat. No. 4,860,749. In these cases also, atrial and ventricular rates or intervals are compared to one another in order to distinguish sinus and pathological tachycardias.

Another approach to the detection of and discrimination between pathologic and sinus or normal tachycardias involves the comparison of current electrogram morphologies to a stored library of morphologies in the manner shown for example in the U.S Pat. No. 4,523,595. In such systems, the suspect electrograms are continuously digitized and compared against the reference digitized electrograms to find the closest fit and diagnose the suspect rhythm.

The aforementioned discussion reflects the development in the art of the detection and discrimination of spontaneously occurring atrial and ventricular tachycardias. In the field of dual chamber atrial synchronous heart pacemakers, such as multiprogrammable DDD pacemakers, the generation of ventricular stimulation pulses ensues after an AV delay time following the detection of an atrial or P-wave signal. The ventricular stimulation rate varies within a relatively wide range from a programmable lower rate, such as 50-75 beats per minute, to a programmable upper rate, such as 100-140 beats per minute. The ventricular stimulation rate may track the sensed atrial P-wave rate up to the upper rate limit whereupon synchronization may be lost periodically, the pacemaker exhibiting a pseudo-Wenckebach behavior, as described in Adams U.S. Pat. No. 4,059,116, for example.

If retrograde conduction exists in the patient's heart, each ventricular stimulus may evoke a depolarization that is conducted back to the atrium, causing it to contract. The atrial sense amplifier may respond to the corresponding P-wave, and in turn, trigger the generation of a ventricular stimulus at or near the upper rate limit of the pacemaker. This behavior of the pacemaker is referred to as "pacemaker-mediated tachycardia" or PMT. In order to prevent PMT, most DDD pacemakers include a programmable post ventricular atrial refractory period that the physician may extend to cause the atrial sense amplifier to ignore the retrograde induced P-wave. However, lengthening the refractory time, in effect, reduces the upper rate limit and is, therefore, disadvantageous to the patient. Another proposal has been to provide timing windows for detecting the closely-coupled retrograde P-wave and to switch the pacing mode of operation to a single chamber mode, such as VVI pacing. In U.S. Pat. No. 4,802,483, circuitry is provided to improve the transition between VVI pacing and DDD pacing to avoid synchronization to atrial activity triggered by retrograde transition. In DDD pacemakers, it remains desirable to provide a reliable method and apparatus for distinguishing atrial activity triggered by retrograde conduction from normal physiologic atrial activity and to provide an appropriate response mode.

SUMMARY OF THE INVENTION

It is an object of the present invention to distinguish among normal sinus tachycardia, pathologic supraventricular tachycardias, and ventricular tachycardias.

It is a further object of the present invention to provide a method and apparatus for discriminating among the various normal and pathologic tachycardias and for providing appropriate therapies for the treatment thereof.

It is the further object of the present invention to discriminate anterograde from retrograde atrial activation to avoid the induction of pacemaker mediated tachycardias by dual chamber pacemakers.

The above objects of the present invention are achieved by a method and apparatus employing the near-field (i.e., closely-spaced) bipolar electrode sensed, atrial P-wave and ventricular R-wave electrograms to trigger storage in memory of concurrently occurring far-field, unipolarly sensed, atrial and ventricular electrograms, processing a certain number of the far-field electrograms, and comparing the electrograms against previously stored reference or control electrograms or other criteria to discriminate among various cardiac arrhythmias on the basis of their atrial and/or ventricular morphologies.

These objects of the present invention are realized in a method and apparatus which provides for: continuous measurement of the atrial and ventricular cycle lengths of the patient's cardiac rhythm via bipolar detection electrodes situated in or on the atrium and ventricle of the patient's heart, respectively; comparison of the atrial and/or ventricular cycle lengths to respective atrial and ventricular tachycardia detection intervals; comparison of the atrial and ventricular cycle lengths to one another and, if they are equal, enabling of atrial and ventricular far-field sense amplifiers coupled to at least one of the ventricular or atrial electrodes and a common remote electrode to simultaneously detect the far-field atrial and ventricular electrograms; and examination of the characteristics of the far-field atrial and ventricular electrograms of a series of one or more such electrograms to determine if they reflect by their morphological characteristics a specific normal or pathologic rhythm.

More particularly, the method and apparatus of the present invention provides for: enabling the atrial and ventricular far-field sense amplifiers continuously upon detection of tachycardia by the measurement of the cycle lengths; digitizing the far-field electrograms and applying the digitized signals to respective atrial and ventricular circulating buffers; detecting the corresponding near-field atrial and ventricular depolarizations and, after a pre-selected time delay, transferring the contents of the atrial and ventricular buffers into memory; continuing to collect and transfer a predetermined number of atrial and ventricular far-field electrograms in memory; and comparing certain characteristics of the stored far-field electrograms with characteristics of reference rhythms and classifying the detected tachyarrhythmia accordingly.

Additionally the proposed invention provides for placing the system in a "learn" mode while the patient is in sinus tachycardia and/or an induced or spontaneously occurring pathological tachyarrhythmia, causing it to repeat the data collection operation described above in order to store in memory control or reference electrograms. In this fashion, digital representations of baseline normal and pathologic arrhythmia electrograms can be created. Suspect tachyarrhythmia electrograms are tested against the reference electrogram set by pairing the suspect electrogram with each of the reference electrograms and performing a least squares linear fit of the paired electrogram sample sets and evaluating the correlation coefficient of the computed linear regression. (Suspect Electrogram=A+B.Reference Electrogram.) The correlation coefficients for the curve fits are used as a programmable measure of morphology match.

As an example, the physician may choose to have the device learn sinus tachycardia. Then, if a suspect rhythm correlates highly it is declared sinus and ignored. If it correlates poorly, it is declared pathologic and treated. Thus all non sinus tachycardias are likely to be detected and treated. Alternatively, the physician may have the device learn the specific waveform of the patient's primary clinical tachyarrhythmia. Then if the waveform of the suspect tachycardia correlates highly, it is declared to be the target rhythm and treatment is instituted. If the waveform correlates poorly, it is declared to be other than the target rhythm and is left untreated. If multiple arrhythmia reference electrograms have been established, the correlation coefficients can be used to institute different therapies for the suspect rhythm depending upon which reference electrogram provides the best correlation value.

In the context of pacemaker mediated tachycardias, whenever the pacemaker attempts to pace the ventricles at elevated rates the far-field atrial electrogram can be evaluated against reference sinus rhythm far-field atrial electrograms in order to prevent pacing the ventricles at rapid rates in response to non sinus atrial tachyarrhythmias or retrograde atrial activation. This would then allow the physician to safely program short post-ventricular atrial refractory periods to permit better upper rate limit performance and to enhance arrhythmia detection processes.

BRIEF DESCRIPTION OF THE DRAWINGS

The above and other objects, advantages and features of the invention will become apparent when considered with the following specifications and accompanying drawings wherein:

FIG. 3 is an illustration of the atrial and ventricular electrograms derived from the electrodes configurations illustrated in FIG. 1 and processed in FIG. 2;

FIG. 10 illustrates a set of equations used to perform linear regression between the samples $Y_n$ of a suspect EGM and the samples $X_n$ of a reference EGM to yield a correlation coefficient r which is a measure of the match between the waveforms.

DESCRIPTION OF THE PREFERRED EMBODIMENTS

Figure 1:
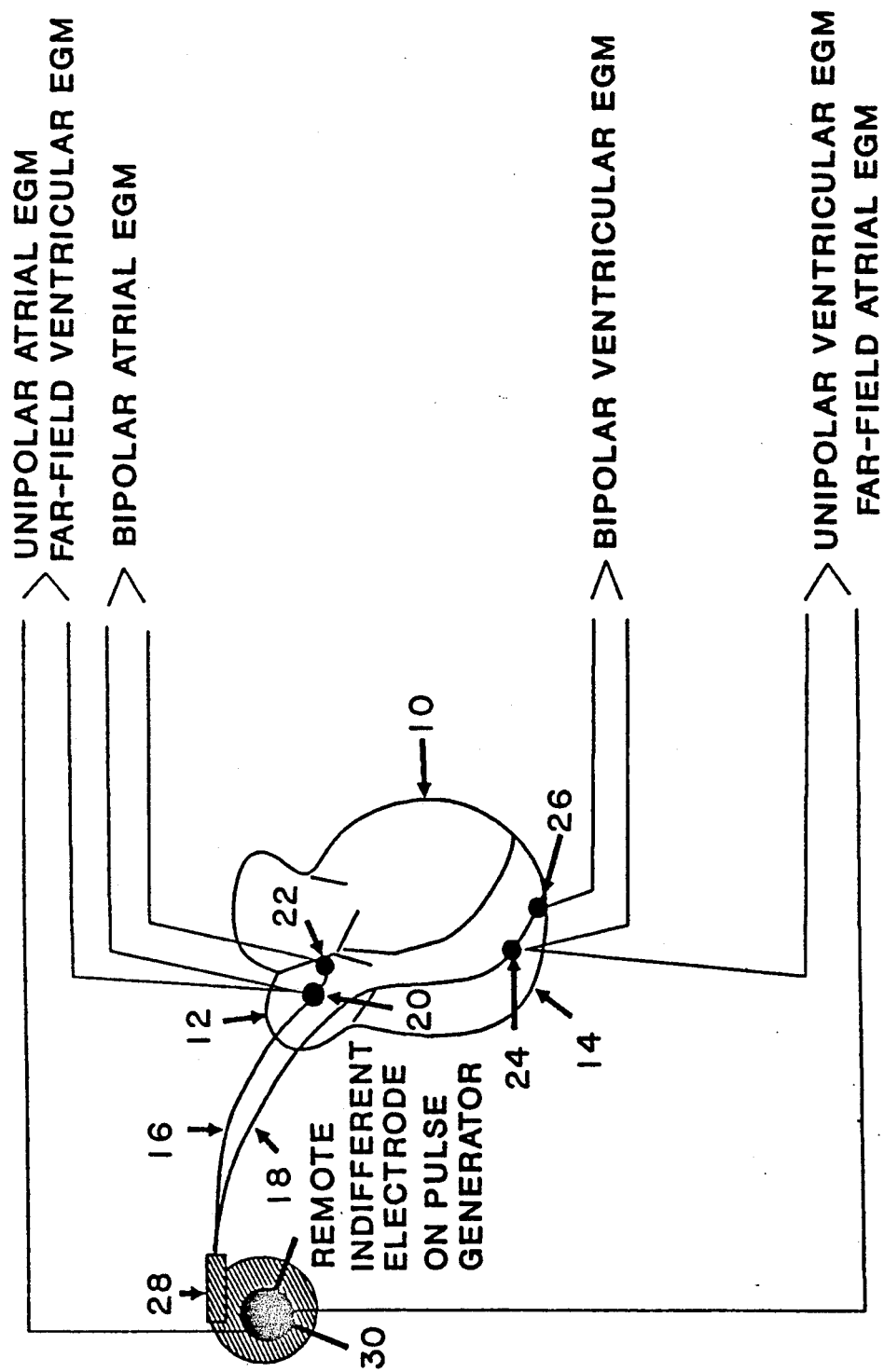
FIG. 1 is a schematic illustration of the bipolar atrial and ventricular electrodes and the remote indifferent electrodes and their arrangement in relation to a patient's heart for sensing the far-field and near-field, atrial and ventricular electrograms.

As stated hereinbefore, the present invention contemplates at least two embodiments which may be practiced in single or separate devices. Both embodiments encompass the concepts illustrated in FIGS. 1–7 and 9 in whole or in part. The first embodiment illustrated in particular with respect to FIGS. 4–7 involves the detection and discrimination of pathologic tachyarrhythmia and the treatment of same by a system of the type depicted and described in reference to FIG. 9. The second embodiment illustrated in particular with respect to FIG. 8 and employed in a portion of the system depicted in FIG. 9 is directed to the prevention and control of pacemaker mediated tachycardias due either to retrograde conduction or tracking of non-sinus atrial tachycardias in dual chamber, antibradycardia pacemakers.

An understanding of the operational modes of the first embodiment of the present invention is facilitated by a brief discussion of the physiology of the heart and the theoretical mechanisms of cardiac tachyarrhythmias.

The normal pumping action of the heart results from highly organized electrical activity in the cardiac tissue. Each natural spontaneous heart beat begins with an electrical discharge from the sino atrial node (S-A) located in the right atrium of the heart. This electrical impulse is conducted through tissues which result in the progressive depolarization of the atrial tissue causing it to contract. The contraction forces blood from the atrium through the heart valves into the ventricles. The electrical impulse from the atrium is communicated to the ventricles through the atrio-ventricular node (A-V), which is located on the septal wall dividing the right and left heart. The electrical signal is delayed in this conductive mode for approximately 0.15 seconds and is then transmitted through the His bundle and its branches to the Purkinje fibers which discharge ventricular muscle, causing the ventricles to contract in an organized fashion and pump blood throughout the body. In the healthy heart, this normal sinus rhythm may be repeated between 60 and 120 times per minute. In the diseased heart, however, a number of arrhythmias may occur which disrupt this normal activity. The type of arrhythmias are divided into two groups: tachyarrhythmias, which are generally characterized by heart rates faster than normal, and bradyarrhythmias, which are characterized by heart rates lower than normal.

The characterization and origin of a tachyarrhythmia is of practical significance since the success of drug treatment of such disorders depends to a great degree on the accurate determination goof their origin and cause. In contrast, when cardioversion is selected to treat these disorders, the characterization and origin of the arrhythmia is of less significance. For example, it has been shown that transthoracic DC electrical shock can successfully terminate many different types of tachyarrhythmias. See, for example, *Cardioversion*, B. Lown, Med. Ann. D.C., 38:543, 1969. However, in an implantable device where power source energy and patient tolerance to repeated cardioversion/defibrillation shocks are both limited, it is necessary to draw fine distinctions between types of tachyarrhythmias and to treat the detected tachyarrhythmias with the lowest energy, least painful electrical stimulation therapies. Thus, it is desirable to terminate tachyarrhythmias wherever possible by low energy painless pacing stimuli and, if necessary, increase the aggressiveness of the therapy if the arrhythmia is not pace terminable or accelerates to a nonpace terminable arrhythmia.

Conversely, it is desirable to immediately discriminate the nonpace-terminable and life threatening ventricular fibrillation and unstable ventricular tachycardia, and immediately treat those arrhythmias with cardioversion/defibrillation shock therapies.

Tachyarrhythmias may be characterized further by their location of origin. For example, the origin of supraventricular tachyarrhythmias is in the atria; and its maintenance involves the atria and sometimes ventricles. Ventricular tachyarrhythmias originate and are maintained within the ventricles and sometimes conduct to the atria by a retrograde conduction pathway. A separate group of tachyarrhythmias are called flutter or fibrillation. Flutter is generally characterized by rapid, organized heart activity and, when involving the ventricles, low cardiac output. Fibrillation is characterized by highly disorganized electrical activity that results in virtually no cardiac output when it involves the ventricles. In some patients there may be a progression from an organized tachycardia to fibrillation which will lead to death if the site of the fibrillation is the ventricles. In many patients, ventricular tachycardia precedes the onset of ventricular fibrillation; and if the former can be terminated, generally with small amounts of energies, the latter can be prevented. Some patients exhibit chronic atrial flutter or fibrillation which may be debilitating but does not cause death, and other patients exhibit occasional or paroxysmal attacks of ventricular tachycardias which require cardioversion. See, for example, "Cardiac Arrhythmias," in Current Diagnosis, W. B. Saunders Co., 1977, pp. 377-396, by Douglas P. Zipes, M.D.

Ventricular tachycardias can be converted to sinus rhythm by the application of cardioversion shock or by the application of pacing energy electrical stimulation including rate adaptive or orthorhythmic stimulation as described first in Zacouto U.S. Pat. No. 3,857,399, overdrive stimulation, burst overdrive stimulation rate scanning or any of the other known pacing therapies as described, for example, in Fisher et al, "Implantable Pacers for Tachycardia Termination: Stimulation Techniques and Long-Term Efficacy", PACE, Vol. 9, November December 1986, Part II, pp. 1325-1333. As a general proposition, it is preferable to convert ventricular tachycardias, if possible, to sinus rhythm by application of lower energy stimulation in order to conserve energy of the power sources of the implantable device as well as to maintain patient comfort. Many patients cannot tolerate the pain associated with cardioversion or defibrillation shock therapies loading to dread of the implanted cardioverter/defibrillator. Thus, it is desirable to further distinguish pace terminable from non-pace terminable ventricular tachycardias and program the implanted device to first attempt to restore sinus rhythm through the application of programmed pacing energy therapies of one or more of the types described above.

In this regard, certain ventricular tachycardias, referred to as stable ventricular tachycardias, are more likely to be terminable by pacing therapies than other ventricular tachycardias, referred to as unstable ventricular tachycardias.

Turning now to FIG. 1, the relationship of the electrodes disposed in and around a patient's heart 10 for picking up the atrial and ventricular, unipolar (far-field) and bipolar (near field) electrograms (EGMs) is shown. The heart 10 includes an atrial chamber 12 and ventricular chamber 14 within which or onto which atrial and ventricular leads 16 and 18 are implanted so as to dispose relatively closely-spaced bipolar electrode pairs 20, 22 and 24, 26 in order to pick up the heart's atrial and ventricular EGMs. The leads 16 and 18 are coupled to a pulse generator system 28 which is disposed outside the heart under the patient's skin in the normal fashion and which carries a remote indifferent electrode 30 on the pulse generator case. The implanted pulse generator 28 may incorporate the system elements depicted in the block diagram of FIG. 9 to be described in detail later.

The bipolar electrode pairs 20, 22 and 24, 26 and their associated leads 16 and 18 may take the form of conventional bipolar pacing leads wherein the inter-electrode spacing between each electrode of each pair is preferably less than 3.0 centimeters, optimally in the range of between 0.5 centimeters and 1.0 centimeters. Such bipolar electrode spacings have been known in the art since bipolar pacing and electrogram sensing leads first became commonly used in the 1960's.

When electrical signals are sensed across the electrodes 20, 22 and 24, 26 constituting the bipolar electrode pairs, they are respectively referred to as the bipolar atrial and ventricular EGMs by virtue of the location of the electrodes in conjunction with the atrium and ventricle of the patient's heart. Normally, the bipolar electrode pair 20, 22 is employed to sense the atrial P-wave whereas the ventricular electrode pair 24, 26 is employed to detect the ventricular depolarization waves (or QRS complex), commonly referred to as the R-wave. However, inasmuch as the P-waves and R-waves are conducted throughout the heart, and thereby pass by each electrode of each electrode pair, it is possible to detect the attenuated P-wave and R-wave signals by coupling suitable sense amplifiers across each electrode pair. However, normally, pacing systems ar designed to employ the atrial leads to detect the atrial electrogram or P-wave and ventricular leads to detect the ventricular electrogram or R-wave and to avoid detecting any other component of the EGM. In the context of the present invention, when reference is made to the bipolar atrial and ventricular EGMs it will be understood that the signals to be detected and emphasized are the P-wave and R-wave, respectively. The close spacing of the bipolar electrode pairs 20, 22 and 24, 26 is designed to optimize the detection of the P-wave and the R-wave, respectively, and to attenuate the detection of the R-wave and P-wave, respectively.

FIG. 1 also illustrates the use in accordance with the present invention of a remote indifferent electrode 30 on the pulse generator 28 in conjunction with the proximal electrodes 20 and 24 (or the distal electrodes 22 and 26) across which unipolar atrial and ventricular EGMs and the far-field ventricular and atrial EGMS, respectively, can be detected. In accordance with the present invention, it is desirable to detect in on chamber (such as the atrium) the far-field EGM representing the depolarization wave form of the other chamber of the heart (such as the ventricle). Thus, by connection to suitable sense amplifiers, the depolarization wave form signal appearing across the electrode pair comprising electrodes 20 and 30, for example, can detect the far-field R-wave. Conversely, a suitable sense amplifier coupled across the electrodes 24 and 30 ma be employed to detect the far-field P-wave. These far-field EGMS derived in a fashion illustrated in FIG. 1 are preferably used in the present invention to discriminate pathologic tachyarrhythmia from normal sinus tachycardia and/or to distinguish a natural atrial tachycardia from a PMT (caused by the retrograde conduction of the pacemaker-triggered ventricular depolarization) and to provide appropriate therapies to the patient s heart to treat the detected tachyarrhythmia or to modify the operation of the dual chamber pacemaker to avoid PMT.

Figure 2:
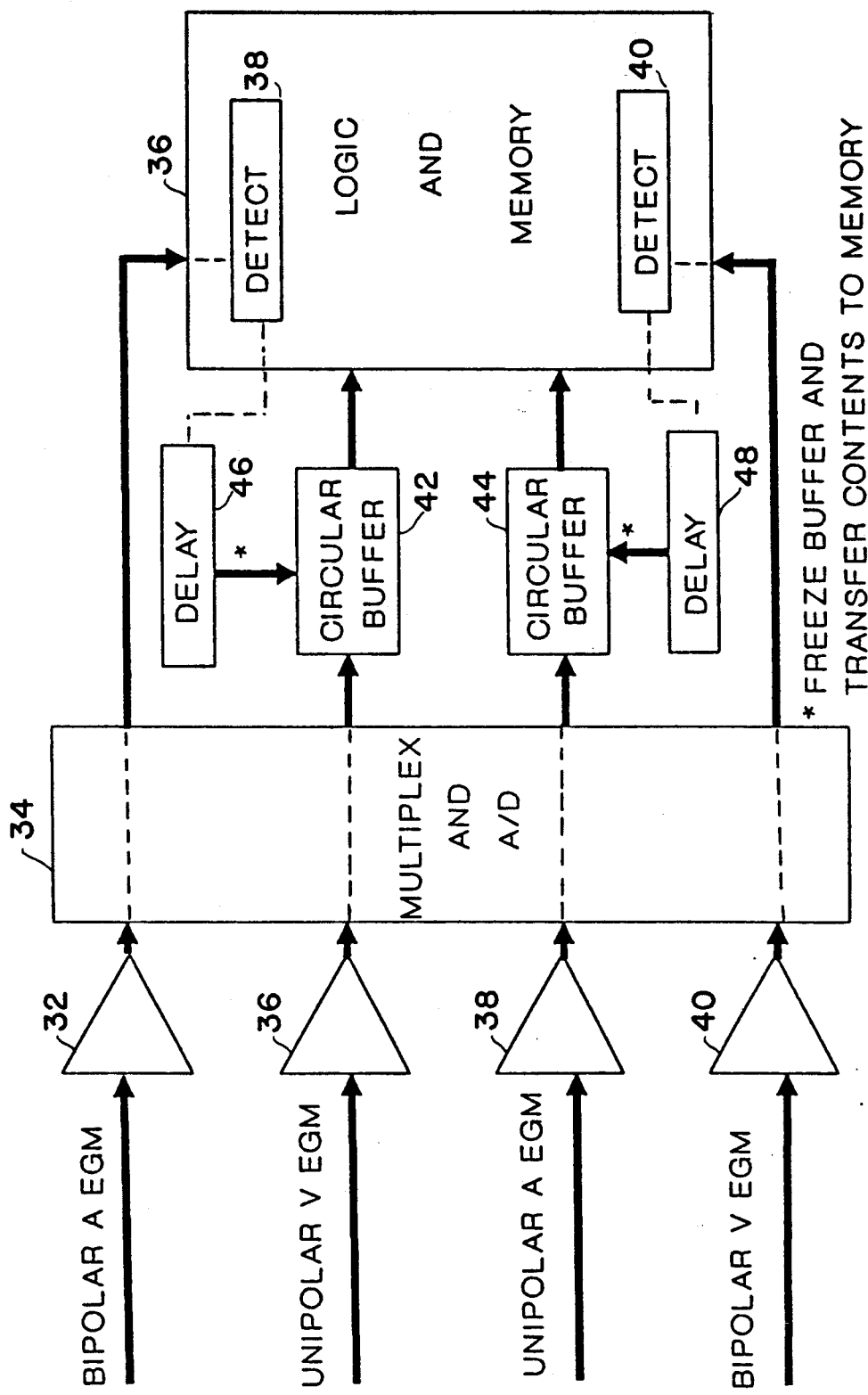
FIG. 2 is a schematic block diagram of the logic and detection circuitry for processing the atrial and ventricular electrograms in order to distinguish pathologic tachyarrhythmias from sinus or normal tachycardias.

The block diagram of FIG. 2 depicts how the atrial and ventricular near-field and far-field EGMs picked up across the electrodes illustrated in FIG. 1 are processed in accordance with the routines illustrated in FIGS. 4-8. FIG. 3 depicts the EGMs as picked up from the electrodes illustrated in FIG. 1 and the storage of the far-field EGMs for morphology analysis.

In FIG. 2, the bipolar atrial EGM detected across the bipolar electrode pair 20, 22 of FIG. 1 is amplified in sense amplifier 32 and applied to a multiplexer and A-D converter 34. Similarly, the unipolar ventricular electrogram detected across electrodes 24 and 30 of FIG. 1 is amplified by a sense amplifier 36 and applied to in further input of the multiplexer and A-D converter 34. In like fashion, the unipolar atrial EGM and bipolar ventricular EGMs are amplified in sense amplifiers 38 and 40, respectively, and applied to further inputs of the multiplexer and A D converter 34.

Figure 4A:
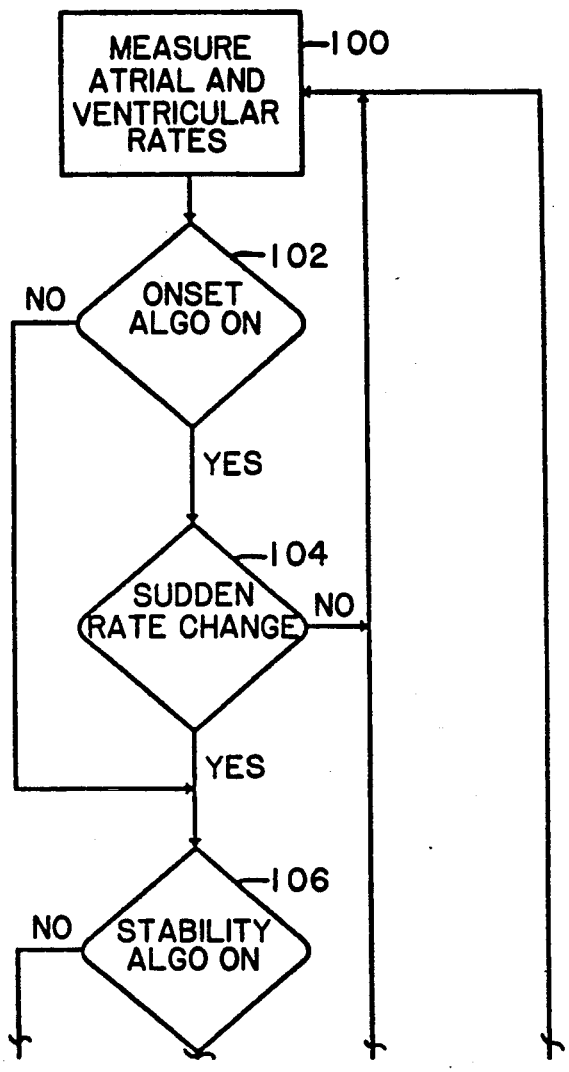
FIG. 4 is a flow diagram of a routine suitable for use in this invention and illustrating tachycardia detection by rate, onset and stability analysis goof the near-field electrograms, which, when satisfied, trigger the morphology analysis of the far-field electrograms.
Figure 4B:
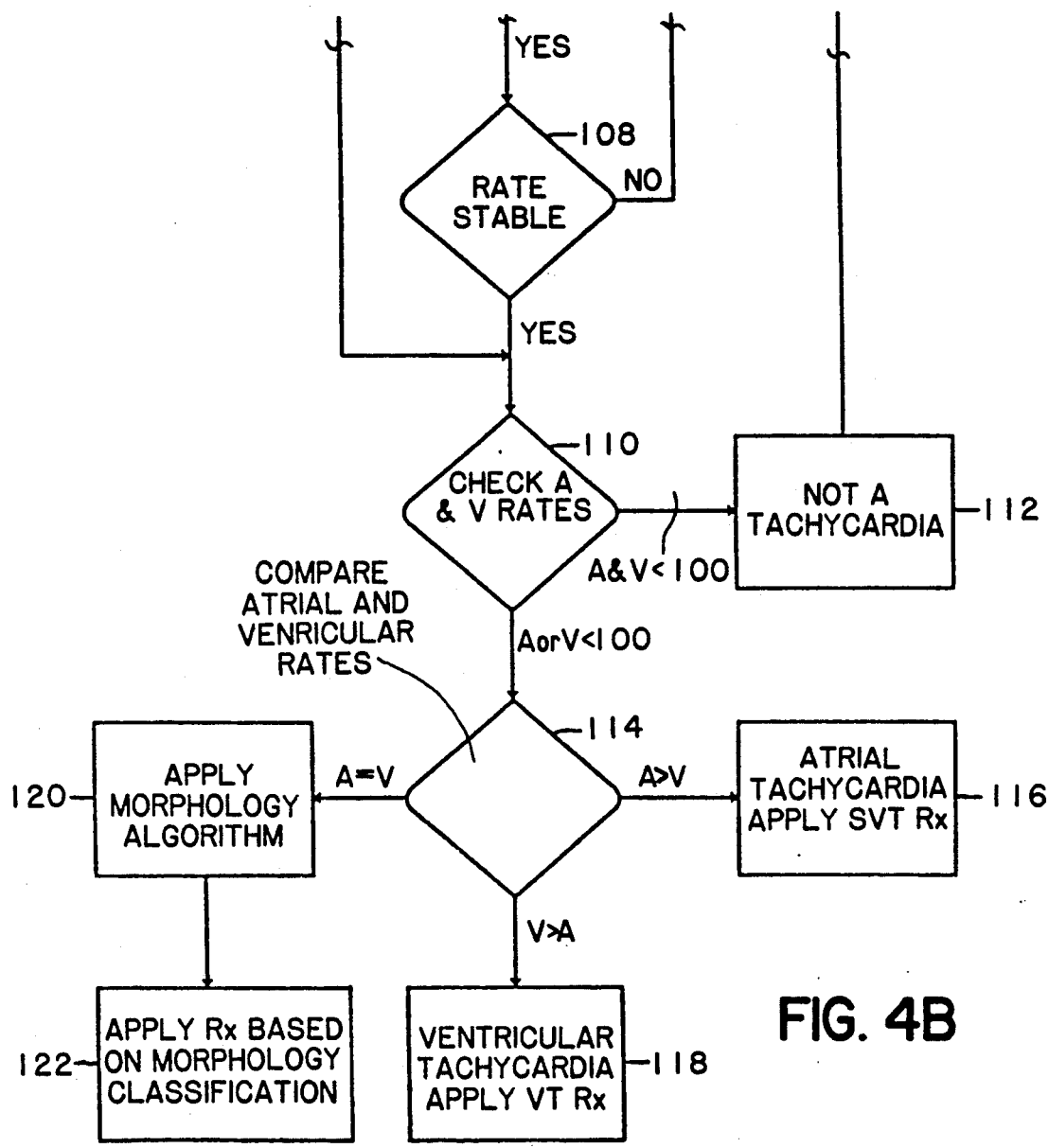

The amplified and digitized bipolar atrial EGMs are applied by multiplexer and A-D converter 34 to the logic and memory block 36 which contains within it a detection logic block 38 for detecting atrial tachycardias in accordance with the algorithm illustrated in FIG. 4. In a similar fashion, the amplified and digitized bipolar ventricular EGMs are directed to the logic and memory block 36 by the multiplexer and A-D converter 34, and detection logic 40 detects the existence of a ventricular tachycardia. Atrial tachycardias are those tachycardias that originate in the atrium and are characterized by too fast an atrial rate of recurrence of P-waves, and ventricular tachycardias similarly are those which originate in the ventricle and are characterized by too high a rate of recurrence of R-waves.

The amplified bipolar electrograms described above may alternatively not be digitized but instead applied to conventional analog pacemaker sensing circuits which detect repeatable characteristics of the P- and R-waves as is well known in the art.

The amplified and digitized, unipolar ventricular and atrial EGMs are passed through the multiplexer and A-D converter 34 and applied to circular buffers 42 and 44, respectively. The multiplexer and A-D converter 34 is conventional in the art and accomplishes the sampling (at 64–256 samples/second, for example), conversion of the sampled analog amplitude of the EGM wave form and the transfer of the sampled digitized data to buffers 42 and 44. The unipolar, or far-field, EGM data stored in buffers 42 and 44 is continuously updated as each successive stream of data entering the buffer replaces the data previously stored therein in a manner which is also conventional in the art. However, in the event that a tachycardia is detected by detection logic 38 and/or 40, the contents of the circular buffers 42 and/or 44 are frozen and transferred into memory after selectable delays 46 and 48, respectively.

Turning now to FIG. 3, the wave forms depicted therein illustrate tracings of the atrial and ventricular EGMs or P and R-waves as they appear across the four electrode pairs employed to develop the four EGM signals applied to the sense amplifiers 32–40 of FIG. 2. At time $t_1$, an atrial depolarization or P-wave originates in the atrium, and the resulting bipolar atrial EGM depicted in tracing A has the appearance normally associated with a bipolar P-wave. The signals illustrated in tracings B, C and D differ in each instance from the tracing of the P-wave illustrated in tracing A and from each other. Note that the P-wave is so attenuated by the closely spaced ventricular electrodes 24, 26 and sense amplifier 40 that it is hardly apparent in tracing C.

Similarly, at time $t_2$, a ventricular depolarization or R-wave occurs, and the signal depicted in tracing C is reminiscent of the classic bipolar QRST complex, or R-wave. The signals as depicted in the tracings A, B and D differ substantially from the signal depicted in tracing C.

Tracings A and B of the atrial EGM and C and D of the ventricular EGM are of particular interest to the present invention. The bipolar atrial and ventricular EGMs of tracings A and C may be easily processed to detect the rate of recurrence by measurement of the intervals between peak amplitudes or slew rates of successive P-waves and R-waves. By tracking the AA and VV intervals or cycle lengths (and optionally the suddenness of onset, rate stability and/or sustained high rate), a tachycardia can be detected. However, it becomes difficult to determine whether or not the tachycardia reflects a more or less normal response to the patient's emotional state or increased level of exercise or is pathologic in origin. Discrimination between stable and unstable ventricular tachycardia may be critical to the prescription of the appropriate therapy. In the context of a staged therapy device, where the appropriate therapies may range from less aggressive pacing stimuli to highly aggressive electroshock therapy, it is desirable to prevent the application of a more aggressive therapy to a tachyarrhythmia condition than is warranted in order to lessen the chance of accelerating the tachyarrhythmia from a benign to a dangerous condition, to avoid applying uncomfortable shocks to the patient and to preserve electrical energy in order to prolong the useful life of the device. In the context of the dual chamber pacemaker in a patient whose heart condition occasionally allows retrograde conduction, it is desirable to distinguish retrograde conducted atrial depolarizations from natural high rate atrial depolarizations again in order to avoid inducing an arrhythmia and making the patient uncomfortable by sustained pacing at the pacemaker's upper rate limit.

In accordance with the present invention, once the rate discrimination criteria are satisfied, the far-field atrial and ventricular EGMs are focused on to provide the morphology discrimination In reference to FIGS. 2 and 3, this is accomplished by thereafter transferring the contents of the circular buffers 42 and 44 into memory within block 36 each time a bipolar P-wave and R-wave is detected by detection logic blocks 38 and 40 such that on each atrial and ventricular event, the far-field atrial and ventricular EGMs are stored for a predetermined number of events. Thus, in reference to FIG. 3, at time $t_1$ the detection of the bipolar atrial EGM in tracing A causes the transfer of the contents of circular buffer 42 into memory within block 36 for a predetermined time window established by delay 46. The time window is illustrated in tracing B as extending forward and backward in time from the peak of the P-wave illustrated in tracing A at time $t_1$.

Similarly, the R-wave depicted in tracing C at time $t_2$ is detected by detection logic 40 which triggers the storage of the digitized sampled far-field ventricular EGM in circular buffer 44. In like fashion, the delay 48 effects the storage of the sampled and digitized data of the far-field ventricular EGM for a time windrow preceding and following the peak of the bipolar R-wave. It will be understood that in reference to FIG. 3 that although the analog signals are depicted for ease of illustration, the signals actually within the circular buffers 42 and 44 are digitized data bits representing the instantaneous amplitudes of the EGMs at each sampling point. Similarly, the digitized values of the bipolar atrial and ventricular EGMs are actually transferred by multiplexer and A-D converter 34 to detection logic blocks 38 and 40, respectively. Before leaving FIG. 3, it should be understood then that the large amplitude excursions of the signals detected in tracings B and D at times $t_2$ and $t_1$, respectively, are digitized and passed through circular buffers 42 and 44, respectively, but are not stored. The shapes of the far-field atrial and ventricular EGMs which are stored in memory are easier to employ in morphology analysis than any of the other signals depicted in the tracings of FIG. 3. The delay effected by the delay circuits 46 and 48, the number of stages in the buffers 42 and 44 and the sampling rate define the length of the windows depicted in tracings B and D of FIG. 3.

Turning now to FIG. 4, the overall tachycardia detection algorithm for performing the analysis of tachyarrhythmias of the first embodiment of the present invention is depicted. The flow chart is similar to the flow chart depicted in the aforementioned Arzbaecher, et al article except that it goes to the morphology discrimination algorithms of FIGS. 5 and 6 in the event that the atrial and ventricular rates are both high. In connection with FIG. 4, the expression "rate," as opposed to interval or cycle length, is employed for convenience of description.

In FIG. 4, at block 100, the algorithm continually measure the atrial and ventricular rates by actual measurement of the intervals between the bipolar atrial and ventricular EGMs or P-waves and R-waves. At each detection of a P-wave and R-wave, the preceding elapsed time or interval is measured and transformed into a rate of recurrence in beats/minute and the algorithm moves to decision block 102 to determine whether or not the onset algorithm is on or off. If the onset algorithm is on, the algorithm moves to decision block 104 where it is determined whether or not the rate reflects a sudden rate change in excess of either a fixed or percentage value of the average rate derived from a certain number of preceding intervals. If no sudden rate change is detected, the measurement of atrial or ventricular rates at block 100 is returned to. If the sudden rate change criteria is satisfied, or if the onset algorithm is "off", then the algorithm moves to the decision block 106 where a determination of whether or not the rate stability algorithm is on or off. If the rate stability algorithm is on, and if the rate is stable, as determined by decision block 108, the algorithm again doubles back to the start to measure successive atrial and ventricular rates at block 100. If the rate stability algorithm is not on or if the rate is stable, then the routine moves to decision block 110 to compare the atrial and ventricular rates against the rate threshold criteria that may be programmed into the device. It will be understood that in actual practice, the specific sequence of steps illustrated in FIG. 4 may be altered in that FIG. 4 as explained so far constitutes merely one illustration of the conventional criteria and analysis of atrial and ventricular rates to obtain some information as to whether or not the rates reflect normal sinus behavior or an arrhythmia.

At decision block 110, the atrial and ventricular rates are checked against programmed rate criteria, in this case, 100 beats/minute. Thus, if the atrial and ventricular rates are below 100 beats/minute, the algorithm concludes that there is neither an atrial nor a ventricular tachycardia (whether or not the onset and stability criteria are satisfied or not) at block 112. No treatment is prescribed and the algorithm doubles back to start at block 100.

However, if either the atrial or the ventricular or both rates are greater than 100 beats/minute, then the algorithm moves to decision block 114 to compare the atrial and ventricular rates to one another. If the atrial rate is greater than the ventricular rate, then it is concluded that an atrial tachycardia exists and that supraventricular tachycardia prescriptive therapies are to be applied at block 116. Similarly, if the ventricular rate exceeds the atrial rate, then the algorithm concludes that it is more likely than not that ventricular tachycardia exists and applies appropriate, programmed ventricular tachycardia prescriptive therapies at block 118.

Figure 5A:
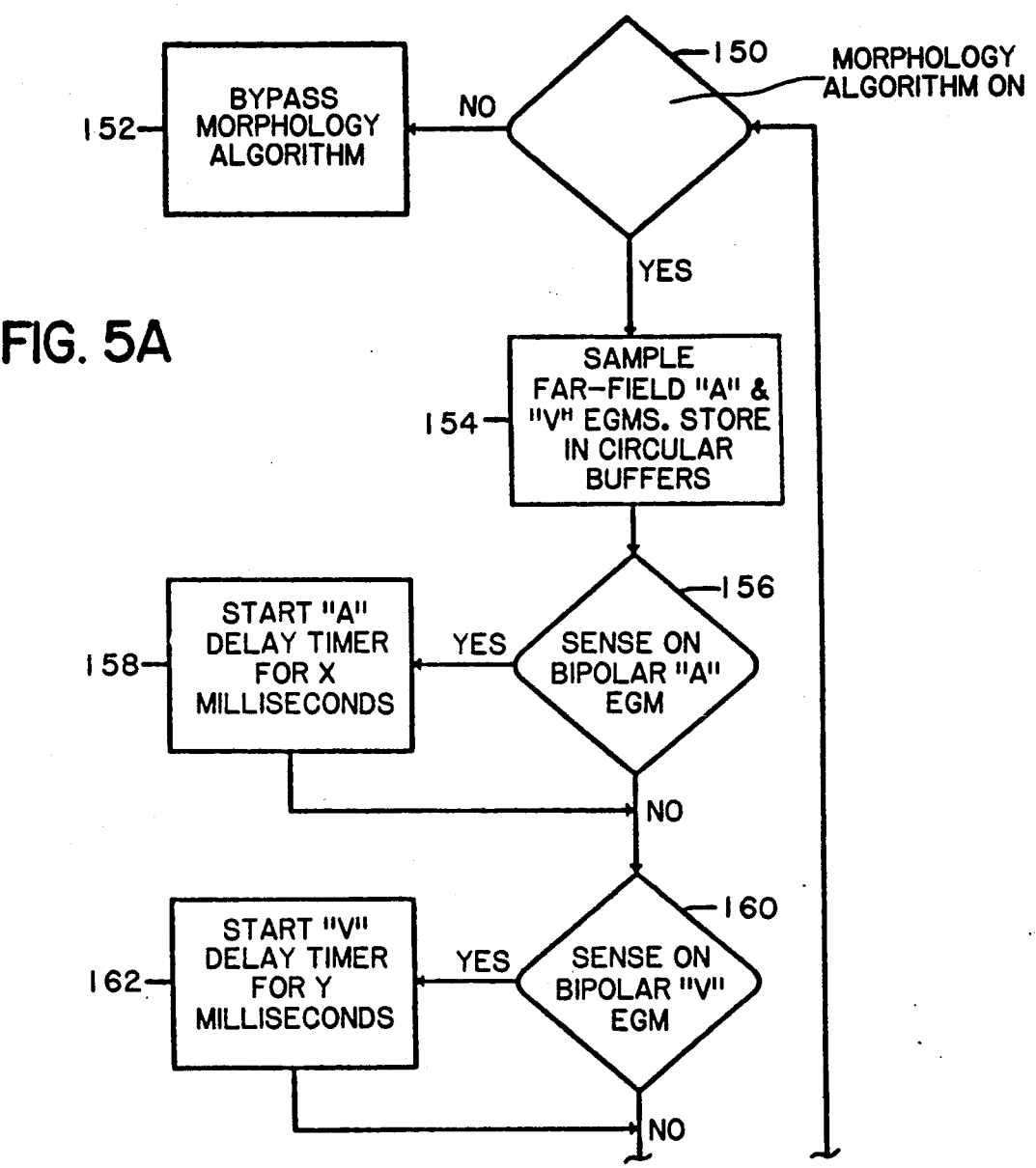
FIG. 5 is a flow diagram of a subroutine directed to the far-field electrogram data collection triggered by the satisfaction of the tachycardia detection algorithm illustrated in FIG. 4.
Figure 5B:
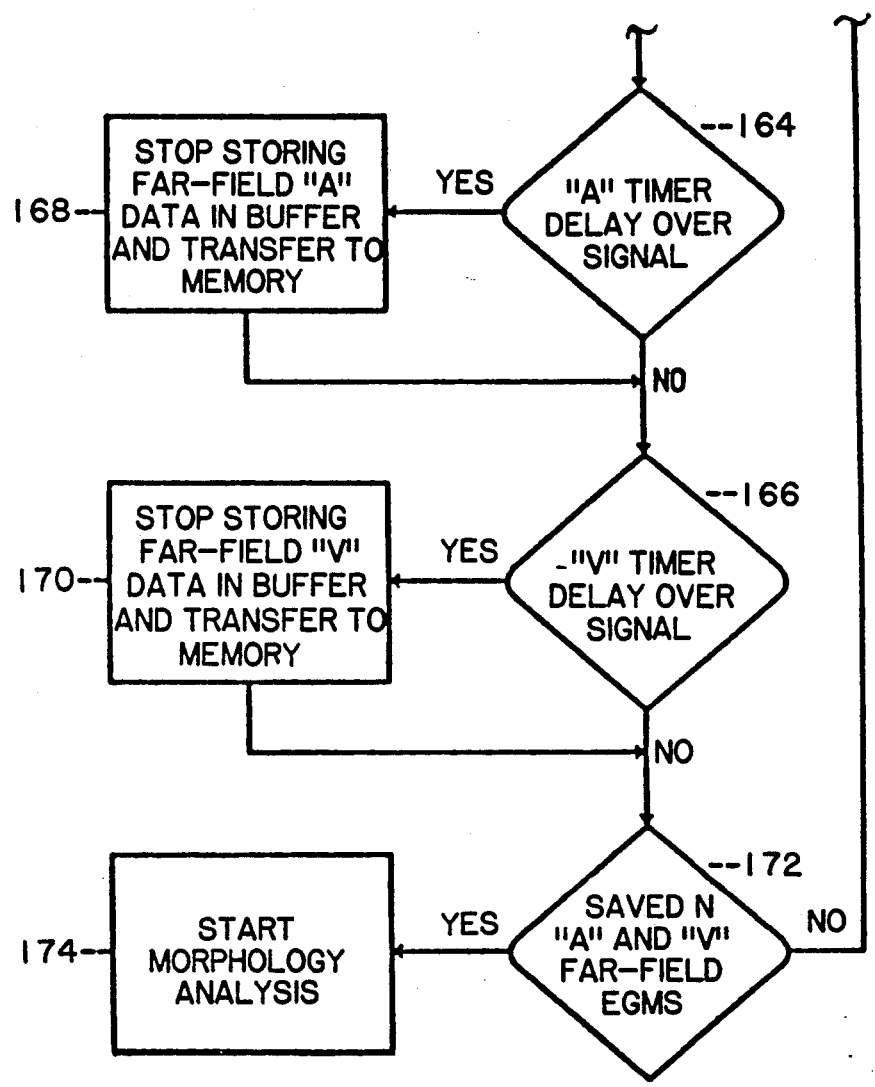
Figure 6:
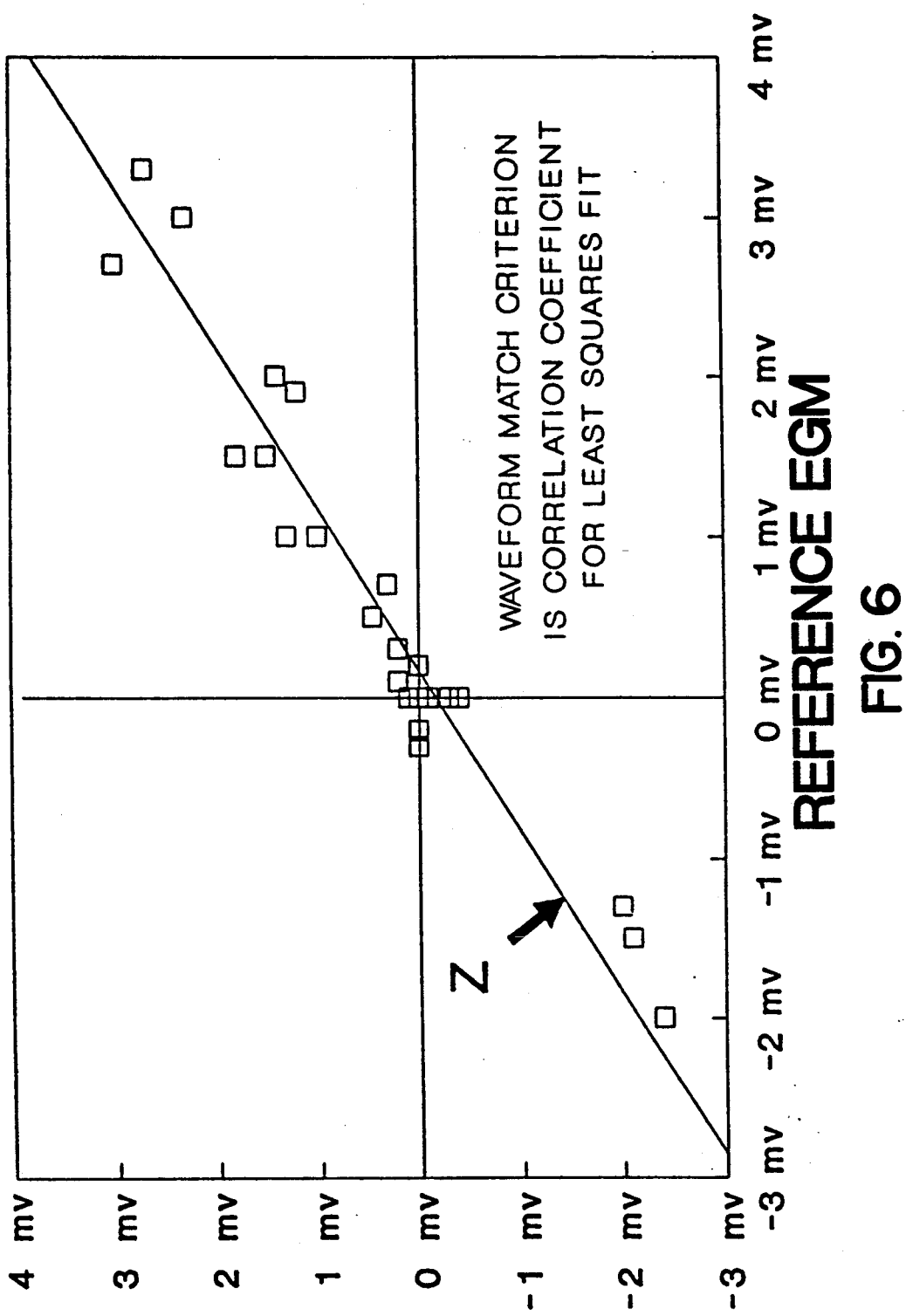
FIG. 6 is a scatter plot illustration of the linear regression technique using reference and suspect electrogram samples preferably employed in the practice of the invention.

If, however, the atrial and ventricular rates are equal within a programmable range of deviation, the algorithm moves to block 120 to apply the morphology algorithm which encompasses the subroutines depicted in FIGS. 5 and 6. Depending upon the results of the morphology algorithm, the system of the present invention contemplates providing in block 122 prescriptive therapies based on the morphology classification.

Although not specifically illustrated in FIG. 4, it will be understood that the rate analysis and the morphology analysis contemplate the analysis of a programmed number of AA and VV intervals in order to satisfy the onset, stability and rate-related criteria and a further programmed number of digitized and stored far-field EGMs for morphology analysis to be described hereafter.

Turning now to FIG. 5. the subroutine of the morphology algorithm far-field EGM data collection algorithm is depicted. This subroutine falls within block 120 of FIG. 4 and relates to the operation of this system depicted in FIG. 2 and the wave form tracings of FIG. 3.

At decision block 150, the question is asked as to whether the morphology algorithm is programmed on or off. If off, the subroutine moves to block 152 to bypass the morphology algorithm analysis and return to block 122 of FIG. 4 to apply those prescriptive therapies which may be programmed by the physician to meet the requirements of the specific patient. For example, in such a system, the physician may have the flexibility of prescribing an aggressive therapy when both the atrial and ventricular rates exceed a certain threshold rate and otherwise satisfy the onset and stability criteria or the physician may prescribe no therapy in the specific instance. In the context of the present invention, it will be presumed that the morphology algorithm is programmed on and the algorithm of the subroutine of FIG. 5 moves to block 154 where the sample far-field atrial and ventricular EGMs (of tracings B and D of FIG. 3) are being stored in the circular buffers 142 and 44 of FIG. 2.

As explained in conjunction with FIGS. 2 and 3, when the morphology algorithm is programmed on and the rate and other criteria are met, the detection of the bipolar atrial EGM at time $t_1$ is sensed and start the atrial delay timer 46. In FIG. 5 at decision block 156, the sensing of the bipolar atrial EGM starts the atrial delay timer in block 158. The atrial delay timer possesses a certain delay time of X milliseconds which in part defines the width of the window depicted in tracing B of FIG. 3.

Similarly, in blocks 160 and 162, the bipolar or near-field ventricular EGM is sensed and starts the ventricular delay timer 48 which after Y milliseconds freezes the buffer and transfers its contents to memory within block 36 of FIG. 2. Both the atrial and ventricular delay timers signal the end of the delay periods at decision blocks 164 and 166, and stop storing the far-field atrial and ventricular data in buffers 46 and 48 and transfer that data to memory within block 36 in blocks 168 and 170, respectively. After N atrial and ventricular far-field EGMs have been stored in memory within block 36, the decision block 172 moves to start the morphology analysis in block 174 in FIG. 7. The flow chart of the subroutine depicted in FIG. 5 may be rearranged to accomplish the described functions, and it will be understood that once the tachycardia detection algorithm of FIG. 4 is satisfied, a morphology algorithm far-field EGM data collection subroutine of FIG. 5 may be commenced but halted before completion if the patient's arrhythmia spontaneously terminates.

Figure 7A:
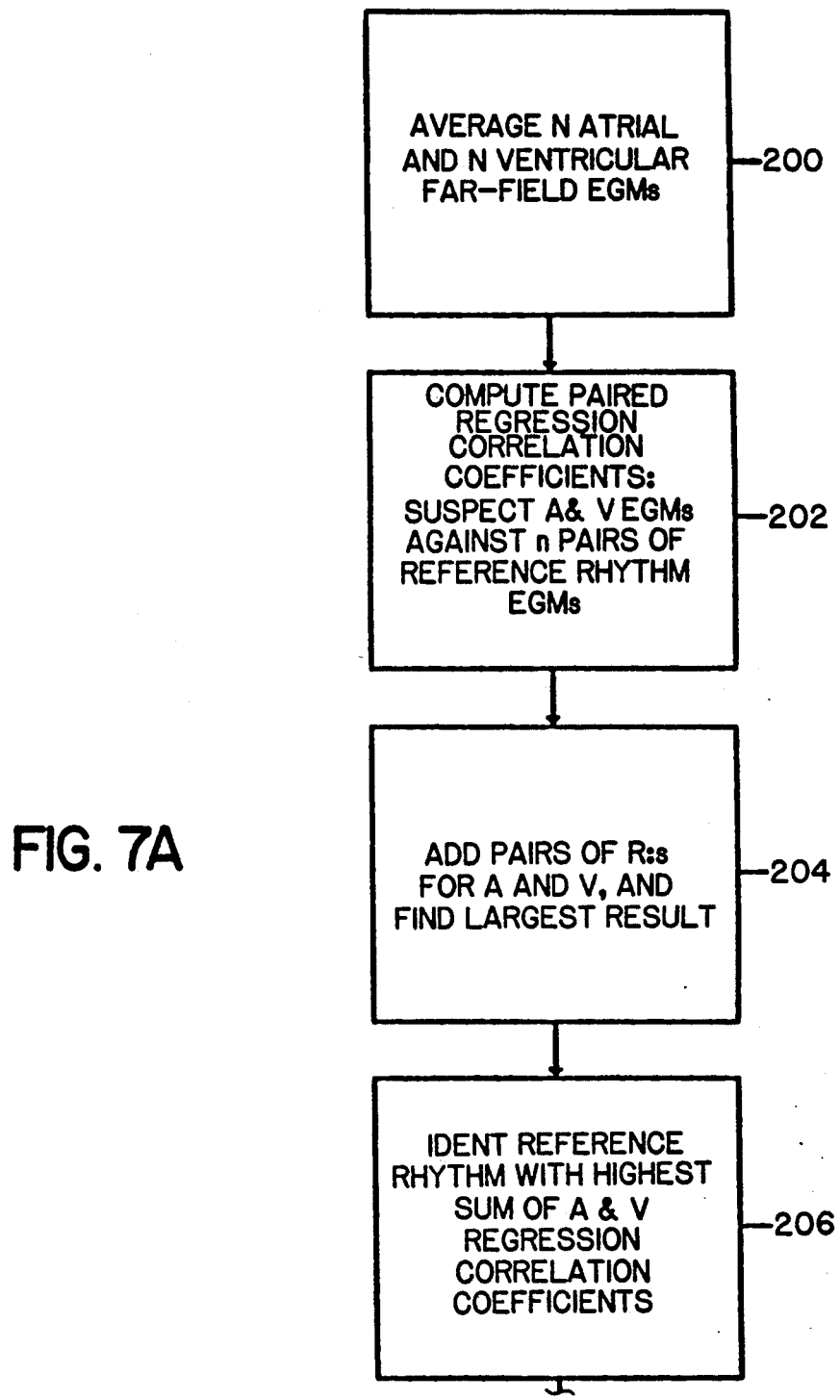
FIG. 7 is a flow diagram of a further subroutine embodying the morphology algorithm arrhythmia classification process employed in the flow diagram of FIG. 4.
Figure 7B:
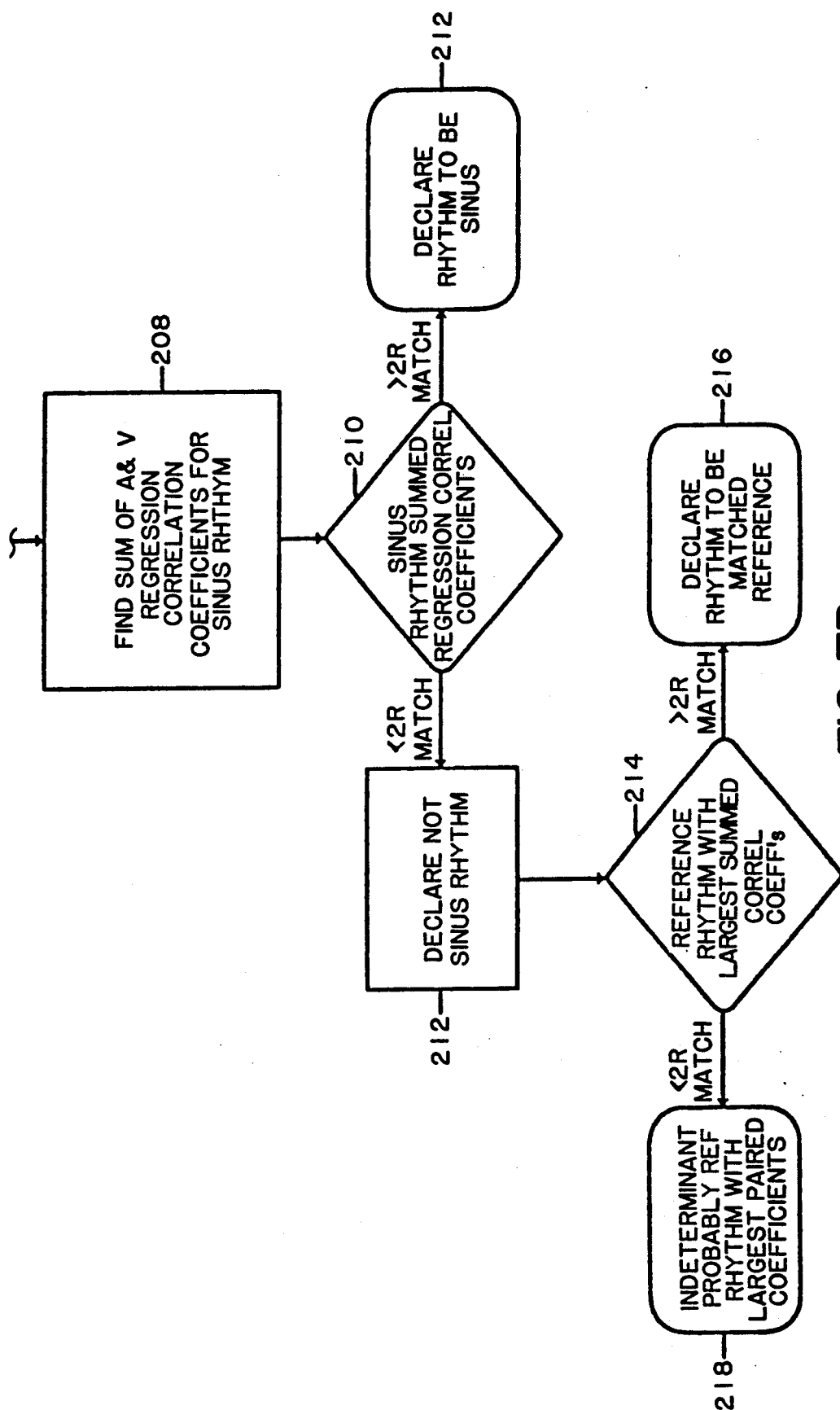

Once the requisite number of atrial and/or ventricular far-field EGMs are stored in memory in block 36, the morphology analysis subroutine of FIG. 7 is commenced. There are many known approaches to pattern recognition and morphology analysis to classify or categorize unknown or suspect wave forms. Physicians are trained in the recognition of arrhythmias and the classifications of specific arrhythmias and discrimination of those arrhythmias from normal or sinus EGMs by study and training and through experience learn to be able to classify EGMs by visualizing a suspect EGM and mentally comparing it against memorized patterns. In working up individual patients, physicians conduct electrophysiologic studies to obtain patient EGMs under a variety of conditions, both natural and induced, in order to diagnose a patient's specific arrhythmia, the causation of that arrhythmia, and the response to applied therapies. In medical device technology, the attempt is made to perform these same functions on a machine basis. Thus, it is known, for example, to work up a patient to store a number of EGMs during normal sinus rhythm at rest and under exercise, as well as induced arrhythmias, to store those reference EGMs in memory and to conduct a comparison between the reference library and suspect EGM samples as taught, for example, in the aforementioned Zibell U.S. Pat. No. 4,523,595. Many different techniques may be employed to conduct that analysis but in the present invention, it is preferred to employ linear regression techniques of the type described, for example, in the book by Sanford Weisberg, *Applied Linear Regression, Wiley Series in Probability and Mathematical Statistics,* John Wiley & Sons, 1985.

In the context of the present invention, it is contemplated that the library of stored morphologies against which the suspect EGM samples are to be compared is collected in the same fashion as described in reference to FIGS. 1, 2, 3, and 5, and stored in referenced RAM memory registers within logic and memory block 36. Thus, the device itself is contemplated to be employed to create the library of reference EGM against which those suspect EGMs which satisfy the detection criteria of FIG. 4 (or FIG. 8 to be described) are compared.

If the suspect EGM were to exactly match one of the reference EGMs in the library of stored reference EGMs, then one would expect that at each sampled point of the two EGMs, the digitized amplitude values would be identical and the difference between the two values would be zero (assuming the polarities are also identical and no baseline shift). Such a situation is seldom if ever realized. Linear regression techniques, and in particular, least squares estimation, facilitate the sampled data comparison between the suspect EGM and the library of reference EGMs to realize an aggregate number ranging from zero (absolutely no matching sample point values) and 1.0 (full matching sample point values), referred to as the correlation coefficient. In practice an intermediate number (such as 0.9) may be employed as a sufficient reference regression correlation coefficient value to declare the suspect EGM as matched to a reference EGM for classification and therapy purposes. Linear regression analysis consists of a collection of techniques used to explore relationships between variables and is especially useful for assessing fits between sample and reference data of the type involved in the present invention. High quality software for regression calculations is available to conduct linear regression fitting of suspect and reference data.

The linear regression technique employing reference and suspect EGM samples may be illustrated by a scatter plot such as that depicted in FIG. 6. In FIG. 6, the X axis is labeled the reference EGM and the Y axis is labeled the suspect EGM. Both axes are marked off in millivolts ranging from −3 mV to 4 mV. The millivolt scales are arbitrarily not identical in order to fit the drawing into an A-4 sized drawing sheet. Normally, the X axis and Y axis millivolt scales would be identical but no harm is caused by making one different from the other. The scatter plot illustration of FIG. 6 is not in fact constructed by the system depicted in FIG. 2 nor is it realized in the morphology algorithm arrhythmia classification subroutine of FIG. 7. It is presented merely to illustrate the concept of employing least squares to arrive at a correlation coefficient for the suspect EGM compared against the reference EGM as described in the aforementioned Weisberg text.

In reference to FIG. 6, the suspect EGM sample point values are plotted as the small squares against the vertical axis. If the suspect EGM were identical to the reference EGM, the suspect EGM sample point values would all fall on the straight line labeled Z. For purposes of illustration, a straight line has been drawn as one would to approximate the distribution of sample point values. Real data will almost never fall exactly on a straight line. The differences between the values of the real data and the straight line values in the aggregate reflect a degree of correlation or lack or correlation between the suspect EGM and the reference EGM sample point values.

Employing the X values as the suspect EGM values, and the Y values as the reference EGM data sampling point values, the equations for arriving at the correlation coefficient value, r, may be expressed as:

$$\bar{y} = a_1 x + a_0 \quad (1)$$

$$\bar{y} = \frac{\Sigma y}{n} \quad (2)$$

$$\bar{x} = \frac{\Sigma x}{n} \quad (3)$$

$$a_0 = \bar{y} - a_1 \bar{x} \quad (4)$$

$$a_1 = \frac{n\Sigma xy - \Sigma x \Sigma y}{n\Sigma x^2 - (\Sigma x)^2} \quad (5)$$

$$r^2 = \frac{[n\Sigma xy - \Sigma x \Sigma y]^2}{[n\Sigma x^2 - (\Sigma x)^2][n\Sigma y^2 - (\Sigma y)^2]} = (\text{Correl. Coef})^2 \quad (6)$$

As stated hereinbefore, the system and algorithms of the present invention do not actually construct the scatter plot illustrated in FIG. 6. Instead, the calculations necessary to arrive at the correlation coefficient is simultaneously performed using the above equations by the software, and those correlation coefficients are further processed in a fashion depicted in the flow chart of FIG. 7. Linear regression techniques advantageously eliminate base line shift o scaling distortions introduced into the electrode system of FIG. 1 as the electrodes mature in the patient's body.

Turning now to FIG. 7, the morphology algorithm arrhythmia classification subroutine which follows from block 174 of FIG. 5 is illustrated. At block 200, the N atrial and ventricular far-field EGMs are averaged by mathematic averaging of the digitized amplitude values of each sample point. Then at block 202, the suspect atrial and ventricular EGM average values (which are characterized in the algorithm as a pair of EGMs) are correlated against n pairs of reference rhythm EGM values to arrive at respective n pairs of regression correlation coefficients for each comparison. Thus, for example, the averaged suspect atrial and ventricular far-field EGM pair is compared against the normal sinus rhythm atrial and ventricular far-field EGM pair and a specific regression correlation coefficients (A and V) ranging from 0 to 1.0, are calculated for the suspect atrial EGM and for the suspect ventricular EGM.

At block 204, the regression correlation coefficients for the atrial and ventricular correlations are added together and the largest value or result is determined. In block 206, that largest result is used to identify the reference rhythm with the highest sum of atrial and ventricular regression correlation coefficients and at block 208, the sum of the atrial and ventricular regression correlation coefficients for sinus rhythm is also identified. These values will be somewhere between 0 and 2.0 and the steps set forth in blocks 206 and 208 may be reversed in sequence or done in parallel. In any case, the value derived in block 208 is compared in decision block 210 against a reference value (designated 2R) and if the sinus rhythm summed regression correlation coefficients exceed 2R, a match is declared between the suspect rhythm and sinus rhythm at block 212. If sinus rhythm is declared, the program exits the subroutine of FIG. 6, and declines to apply any therapy even though the rate onset and stability criteria have been satisfied in FIG. 4 as evidence of a tachyarrhythmia.

Thus, a significant value of the concept of the present invention is to eliminate the delivery of inappropriate therapies in the event that the morphology discrimination of the far-field EGMs evidences a high correlation or fit to normal sinus rhythm. Of course, in the system contemplated, the EGMs may be stored for later retrieval and evaluation by the physician to determine if the programmed correlation coefficient threshold value R is appropriate or not.

Returning to FIG. 6. in the event that the sum of the regression correlation coefficients of the suspect EGM are less than 2R, the algorithm moves to block 212, which merely declares that the analyzed EGMs do not reflect sinus rhythm and moves to decision block 214, which employs the largest summed correlation coefficients derived in block 206 and compares it against a further (or the same) value 2R. If the largest summed correlation coefficients exceed 2R, then, at block 216, the suspect EGM is declared to represent the arrhythmia of the reference EGM against which it most closely correlates. The program reverts to block 122 of FIG. 4 to apply the therapy prescribed for the matched arrhythmia.

However, if the largest summed correlation coefficients identified in block 206 fail to exceed 2R, then at block 218, the arrhythmia is declared to be indeterminate, although probably the reference rhythm with the largest paired coefficients. If that reference rhythm happens to be fibrillation or if the physician programs the device to apply the most aggressive therapy in the event that the arrhythmia cannot be determined then the program exits block 218 and the system applies the prescribed defibrillation therapy in block 122. The system admits the possibility of applying a succession of therapies from lesser to greater degrees of aggressiveness in conjunction with a determination in block 218 of an indeterminate condition. Alternatively, the physician may prescribe staged therapies for recurrences of arrhythmias matched in block 216 until the arrhythmia is terminated and store the successful therapy for initial use at the next episode.

If a stable ventricular tachycardia is diagnosed, then the appropriate therapies to be delivered to the patient's heart by the device depicted in FIG. 9 are low energy, high rate pacing stimuli. However, if ventricular fibrillation or unstable ventricular tachycardia is detected, the appropriate therapy to be delivered is a medium energy synchronized cardioversion shock followed by further, higher energy synchronized or unsynchronized shocks if the initial shock is insufficient to break the tachycardia.

It will be understood that the system of the present invention contemplates data storage and retrieval of the correlation coefficient values, the number and times of occurrences of the episodes, and other data associated with the detection of the arrhythmia and delivery of the therapies for subsequent interrogation and read-out as is known to be conventional in the art.

Figure 8A:
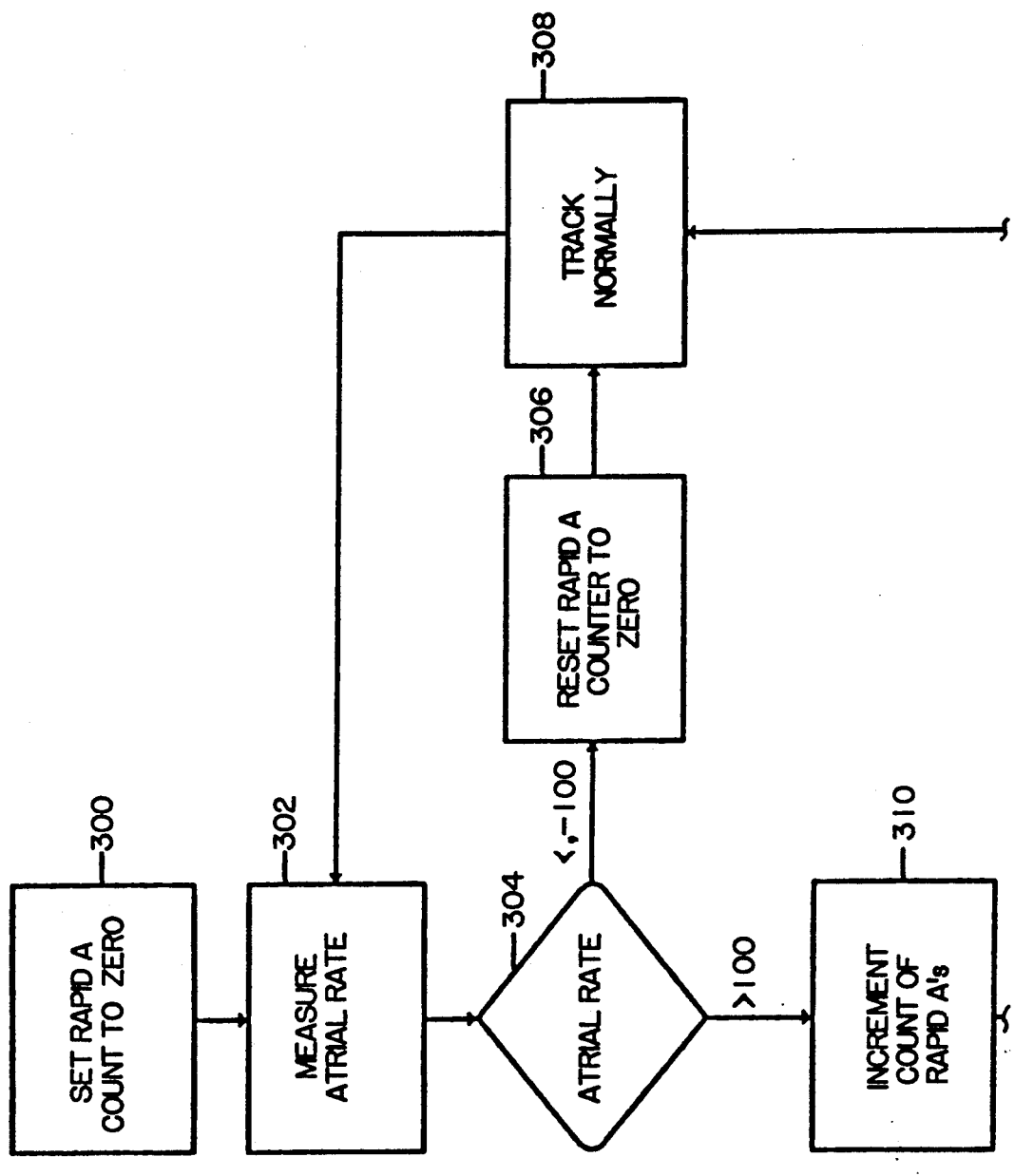
FIG. 8 is an illustration of a further embodiment of the present invention for avoiding the tracking of retrograde and pathologic P-waves for preventing pacemaker-mediated tachycardia in a dual chamber pacemaker system.
Figure 8B:
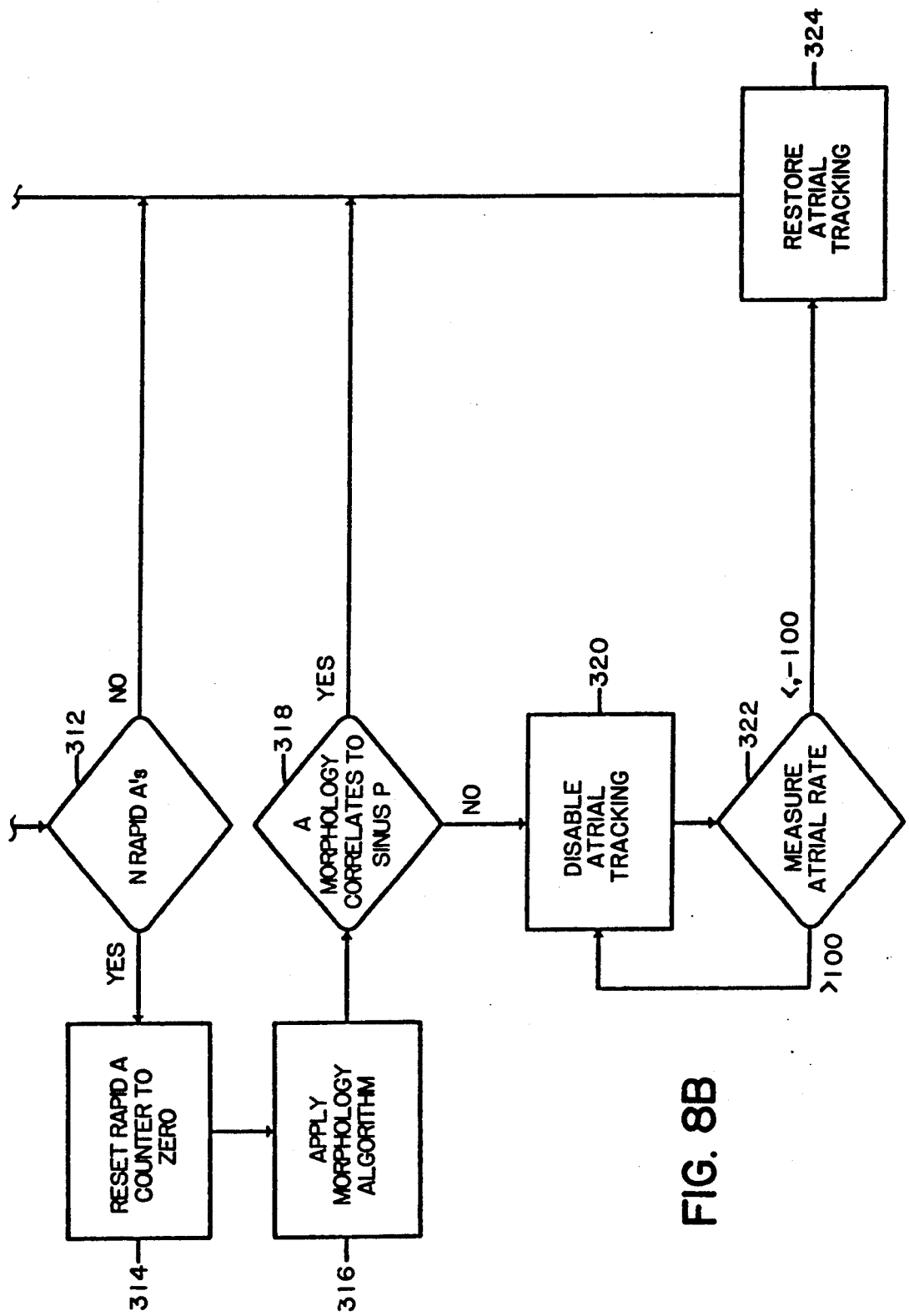
Figure 9:
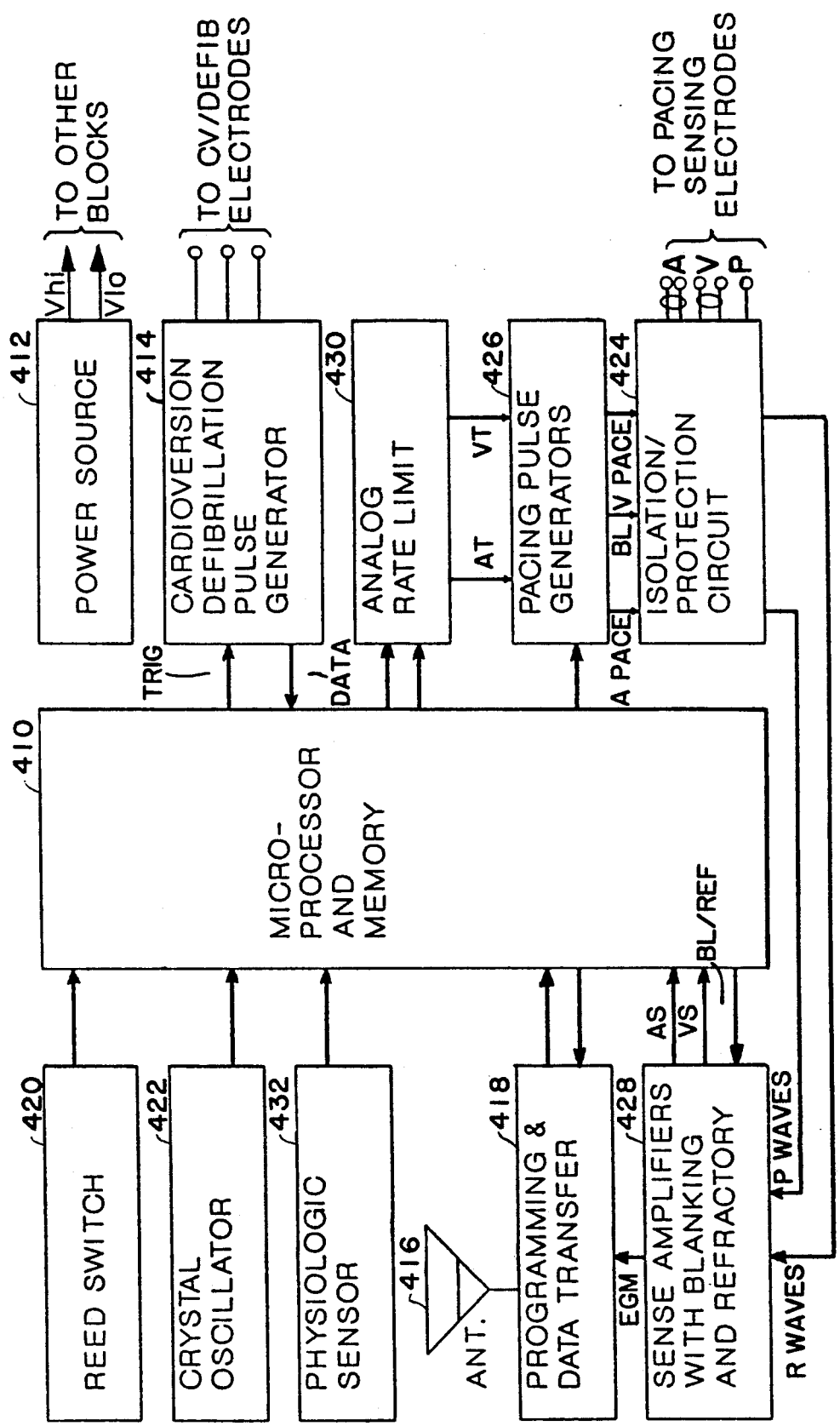
FIG. 9 is a block diagram of a combined antitachycardia and antibradycardia pulse generator within which the methods go and apparatus of the present invention may be practiced.

Turning now to the second embodiment of the invention, FIG. 8 sets forth the flow chart for the algorithm for avoiding the tracking of retrograde and pathologic P-waves in a dual chamber antibradycardia pacemaker. In such pacemakers which employ atrial and ventricular pacing and sensing leads in a pulse generator of the type depicted in FIG. 1, it is desirable to allow the pacemaker to physiologically track the spontaneous atrial events and provide synchronized stimulation in the ventricle when needed as long as the spontaneous atrial rate ranges between a programmable lower rate limit of perhaps 60 beats/minute and a programmable upper rate limit of perhaps 150 beats/minute. However, as stated hereinbefore, it is undesirable that the pacemaker track rapidly recurring P-waves that are either pathologic in origin or are created by the retrograde conduction of a ventricular depolarization, either natural or stimulated, via the AV mode or an accessory pathway of the heart muscle. Where such conditions occur and the pacemaker is continuously triggered to stimulate the ventricle at elevated rates in the absence of an exercise induced need, the patient is rendered uncomfortable, his hemodynamic performance is impaired, and a slight possibility of acceleration of the arrhythmia exists. In the past, various schemes have been developed to avoid this pacemaker-mediated tachycardia condition but they tend to compromise the performance of the device inasmuch as the conditions usually cannot distinguish between a pacemaker mediated tachycardia and a sinus tachycardia. In accordance with the present invention, it is contemplated that the system depicted in FIGS. 1 and 2 in conjunction with the wave shapes of FIG. 3 may be employed to discriminate sinus rhythm P-waves from pathologic or retrograde conducted P-waves by morphology analysis of the far-field atrial EGM.

It should be understood that pacemaker mediated tachycardias can be triggered by sensed P-waves that recur at rates that are less than the upper rate limit of the dual chamber pacemaker. In the context of the present invention it is desirable to discriminate normal and pathologic P-waves at atrial rates less than the upper rate limit so that the physician may program the device to respond appropriately to a sinus rhythm during exercise to provide cardiac output suitable to the patients' needs. For example, the physician may program the device to operate synchronously to an upper rate limit of, perhaps, 175 bpm and separately program the device to test the far-field EGM morphology at a suspect rate of, perhaps, 100 bpm. In such a case, when the atrial rate exceeds 100 bpm, it is considered suspect and the far-field electrogram is examined, at least periodically, to determine if it is sinus or pathologic in origin. If pathologic, the atrial tracking function is disabled until the spontaneous rate falls below the suspect rate. In a DDD pacemaker, for example, the pacing mode would switch to single chamber VVI pacing (with continued atrial sensing) until normal atrial sinus rhythm resumes.

In FIG. 8 at block 300, the program is intialized by setting the rapid atrial count to 0 and thereafter measuring the atrial rate at block 302. At block 304, the measured atrial rate is compared against an upper rate limit of 100 bpm, for example, and as long as it is less than or equal to 100 bpm, the rapid atrial counter is reset again to 0 in block 306 and the pacemaker tracks normally in block 308. A resetting of the rapid atrial counter to 0 in block 306 may occur in the event that the rapid atrial counter has not yet reached its threshold count as described below.

In the event that the instantaneous atrial rate is determined to exceed the suspect rate of 100 bpm, the rapid atrial counter is incremented in block 310. If a succession of measured atrial rates exceed 100 bpm, the count of the rapid atrial counter will be incremented in block 310 and when it reaches N" rapid atrial counts, the morphology algorithm is applied to examine a series of the far-field morphologies of the atrial EGM or P-wave. Thus, in decision block 312, until the count of the rapid atrial counter exceeds N", the algorithm reverts back to block 302 via block 308 to measure the atrial rate. If at any time before the count end is reached, the atrial rate falls below or equal to 100, then the counter is reset at block 306 to 0. However, if the count reaches N", then in block 314, the counter is reset but the program moves to apply the morphology algorithm in block 316. At block 318, the morphology is correlated in the fashion described hereinbefore to a stored sinus atrial electrogram obtained from the patient during a post pacemaker implant evaluation and stored in RAM memory. If the morphology correlates to the stored sinus P-wave, the tracking of the P-waves is declared to be appropriate.

However, if the suspect morphology fails to correlate to the stored reference sinus P-wave morphology, then atrial tracking may be disabled in block 320 until the measured atrial rate again falls below the reference of 100 beats/minute in block 322, whereupon atrial tracking may be restored in block 324.

The algorithm depicted in FIG. 8 thus represents a simple algorithm for conducting a morphology correlation to discriminate high rate sinus atrial depolarizations from retrograde and pathologic P-waves. It will be understood that the morphology correlation may be more sophisticated to compare the atrial morphology against a library of reference P-wave EGM values representing pathologic or retrograde conducted P-waves if they can be induced and stored during a post pacemaker implant workup of the patient by the physician. In such circumstances, a more sophisticated correlation may be conducted although for most purposes, it would be unnecessary to do so. In most instances, the wave shape of P-waves during sinus atrial tachycardia are highly regular and reproduceable. Consequently, it would be only necessary to fit the suspect P-wave against the reference P-wave sample point values and to provide for a correlation value of between 0.8 and 1.0 to declare a match and allow the pacemaker to track the atrial rate.

In addition, other modes of corrective action than mode switching or disabling the atrial tracking may be contemplated including lengthening the post ventricular atrial refractory period (PVARP). In any case, the system would continue to track the atrial rate and analyze the far-field P-waves in accordance with FIG 8. Data storage and retrieval of such episodes may be provided for in order to analyze the arrhythmia and system response.

Before leaving the description of this second embodiment, it should be pointed out its principles can be applied to either unipolar or bipolar atrial synchronous pacing systems along with the remote indifferent electrode. The electrode and pulse generator system depicted in FIGS. 1 and 2 illustrates the bipolar electrode version, although it should be understood that the sense amplifier 38, delay 48, and buffer 44, are not necessary since only the far-field atrial EGM is of interest. To produce the bipolar version only the atrial and ventricular tip electrodes 22 and 26 are employed and the atrial rate and ventricular synchronous stimulation are derived from the unipolar P-wave sensed between the tip electrode 22 and indifferent electrode 30. Again, the far-field atrial EGM for morphology analysis is derived between ventricular tip electrode 26 and indifferent electrode 30.

Reference is now made to FIG. 9 which depicts a block diagram of the major components of automatic implantable device for detecting and treating brady and tachyarrhythmias. It is contemplated that such a device would be implemented in analog and digital microcircuits under the control of a central microprocessor/memory block 41 powered by high (for cardioversion and defibrillation) and low (for the remaining circuitry on pacing therapies) power sources in block 412. The high power pulse generator block 414 would include the cardioversion/defibrillation pulse generator circuitry coupled by output terminals to two or more cardioversion/defibrillation electrodes to apply synchronized cardioversion or unsynchronized defibrillation shocks to the electrodes situated in or about the heart in a manner well known in the art.

It is contemplated that the implantable device depicted in FIG. 9 would function under the control of a resident operating program or software retained in memory within the microprocessor/memory block 410 and would be programmable by a external programmer/receiver (not illustrated in FIG. 9) communicating with the implanted device by radio frequency energy received or transmitted by antenna 416 under the control of the programming and data transmission block 418 and reed switch 420 which is responsive to an external magnet. The programming and data transmitting block 418 would be capable of receiving programming instructions and directing them to the memory within microprocessor/memory block 410 as well as transmitting data stored within the memory block 410 as well as an electrogram representing the patient's atrial and ventricular activity in a manner well known in the pacing art.

The timing of all processing functions, including the determination of atrial and ventricular cycle lengths, is controlled by system clocks within microprocessor/memory 410 driven by crystal oscillator 422 in a manner well known in the prior art of implantable digital pacemakers.

The cardiac signal processing blocks of FIG. 9 include the isolation/protection or interface block 424 which operates to direct atrial and ventricular pacing stimuli from the pacing pulse generator block 426 to respective atrial and ventricular output terminals which in turn are coupled through the pacing leads to the bipolar pacing electrodes situated in or near the atrium and ventricle of the heart as shown in FIG. 1, respectively. In addition, the interface 424 (when unblanked) couples the near-field and far-field atrial and ventricular electrograms to the sense amplifier block 428. Interface 424 is blanked or prevented from passing any signals picked up on the atrial and ventricular pacing/sensing electrodes to the sense amplifier block 428 during short blanking intervals following the delivery of an atrial or ventricular pacing stimulus in a fashion well known in the pacing art.

The indifferent plate electrode of FIG. 1 is coupled to the interface circuit 424 which is used in conjunction with the bipolar pacing/sensing electrodes to provide far field, unipolar signals to the sense amplifier 428 in the manner described hereinbefore. The plate electrode may be one of the cardioversion/defibrillation electrodes, the case of the pulse generator or a separate electrode on or attached to one of the lead bodies.

Furthermore, the interface 424 disconnects or shorts out the pacing/sensing electrodes during the delivery and for a short period after the delivery of a cardioversion/defibrillation shock by application of a control signal to the interface 424 by the cardioversion/defibrillation pulse generator block 414.

The P-wave and R-wave signals transmitted through the interface 424 to the sense amplifiers 428 are amplified and shaped to generate the near-field and far-field atrial and ventricular signals AS and VS, respectively, which are conducted to microprocessor/memory 410 in order to derive the atrial and ventricular cycle lengths, the AV delay interval, and other intervals and rates described hereinbefore to perform the inventive functions of the device. A further signal from a physiologic sensor 432 representative of cardiac or patient activity is also applied to the microprocessor/memory 410 in order to control the bradyarrhythmia pacing rate in the DDDR or other rate responsive mode of operation and to augment detection of tachyarrhythmias.

The microprocessor/memory 410 responds to atrial and ventricular AS and VS signals by generating appropriate atrial and ventricular refractory and blanking intervals which are in turn applied to the sense amplifier block 428 during certain windows of time following each respective AS and VS signal in a fashion well known in the pacing art.

It is contemplated that the system depicted in FIG. 9 may be programmed to operate in any of the known bradycardia single or dual chamber pacing modes. The signal from the physiologic sensor 432 may be employed to modify the atrial and ventricular escape intervals to allow for a certain range of atrial and ventricular pacing depending upon the level of the patient's activity in a fashion well known in the bradycardia pacing art. Suffice it to say, that atrial and ventricular escape intervals established in memory are compared against the atrial and ventricular cycle lengths encountered in the patient and, if a bradycardia condition exists, the microprocessor/memory 410 applies atrial and ventricular pace trigger signals AT and VT through analog rate limiter block 430 to the pacing pulse generator 426 which responds by developing the respective A pace and V pace signals. Analog rate limiter 430 operates to limit atrial and ventricular pacing rates to a safe high rate and effect an appropriate upper rate behavior in the event that the spontaneous atrial rate exceeds the programmed upper rate limit as is described above in relation to the second embodiment of the invention.

Although presently preferred embodiments of the invention have been described, it will be apparent from that description to those skilled in the field to which the invention pertains, that variations of the present embodiments may be implemented without departing from the principles of the invention. Further, as technological advances are made, for example, in developing practical small size, low-cost high voltage components, similar to the advances in the semiconductor field, the principles of the invention may be applied directly to a "universal" implantable device for performing an all-purpose cardiac treatment function.

Accordingly, it is intended that the invention be limited not by the structural or functional elements of the described embodiment, but only as set out in the appended claims.

What is claimed is:

1. A method for discriminating among various normal and pathologic tachycardias of the human heart and for providing an appropriate response thereto comprising the steps of:

sensing the near-field atrial P-wave electrograms from a first pair of electrodes situated in relation to the patient's atrium;

sensing the near-field ventricular R-wave electrograms from a second pair of electrodes situated in relation to the patient's ventricle;

measuring the atrial and ventricular cycle lengths of the patient's cardiac rhythm from the near-field atrial and ventricular electrocardiograms;

determining the existence of an atrial and ventricular tachycardia from said atrial and ventricular cycle lengths;

providing an indifferent electrode remotely spaced from said patient's heart;

sensing the far-field ventricular electrogram from one electrode of said atrial electrode pair and said indifferent electrode;

sensing the far-field atrial electrogram from one electrode of ventricular electrode pair and said indifferent electrode; and examining the characteristics of the far-field atrial and ventricular electrograms of a series of one or more such electrograms to determine if they reflect a specific normal sinus tachycardia or a pathologic arrhythmia.

2. The method of claim 1 further comprising the steps of:

digitizing the far-field electrograms and applying digitized signals to respective atrial and ventricular circulating buffers;

upon determining the existence of a tachycardia, detecting the corresponding near-field atrial and ventricular electrogram and, after a pre-selected time delay, transferring the contents of the atrial and ventricular buffers into memory;

continuing to collect and transfer a predetermined number of atrial and ventricular far-field electrograms in memory; and comparing certain characteristics of the stored far-field electrograms with characteristics of reference rhythms and classifying the detected arrhythmia accordingly.

3. The method of claim 2 further comprising the steps of:

prescribing predetermined therapy regimens for specific arrhythmias; and triggering the application of said predetermined therapies upon the determination that the far-field electrograms reflect corresponding predetermined pathologic arrhythmias.

4. The method of claims 2 or 3 further comprising the steps of:

collecting far-field electrograms representing normal sinus and pathologic tachyarrhythmias from said patient's heart;

storing said normal sinus and pathologic far-field electrograms as a library of reference electrograms; and comparing said suspect far-field atrial and ventricular electrograms to said library of far-field atrial and ventricular reference electrograms to identify the most likely arrhythmia; and providing a therapy appropriate to the identified arrhythmia.

5. The method of claims 1 further comprising the steps of:

collecting far-field electrograms representing normal sinus and pathologic tachyarrhythmias from said patient's heart;

storing said normal sinus and pathologic far-field electrograms as a library of reference electrograms; and comparing said suspect far-field atrial and ventricular electrograms to said library of far-field atrial and ventricular reference electrograms to identify the most likely arrhythmia; and providing a therapy appropriate to the identified arrhythmia.

6. The method of claims 1 or 5 further comprising the steps of:

prescribing predetermined therapy regimens for specific arrhythmias; and triggering the application of said predetermined therapies upon the determination that the far-field electrograms reflect corresponding predetermined pathologic arrhythmias.

7. An apparatus for discriminating among various normal and pathologic tachycardias of the human heart and for providing appropriate therapies for the treatment thereof comprising:

means for sensing the near-field atrial P-wave electrogram from a first pair of electrodes situated in relation to the patient's atrium;

means for sensing the near-field ventricular R-wave electrograms from a second pair of electrodes situated in relation to the patient's ventricle;

means for measuring the atrial and ventricular cycle lengths of the patient's cardiac rhythm from the near-field atrial and ventricular electrocardiograms;

means for determining the existence of an atrial and ventricular tachycardia from said atrial and ventricular cycle lengths;

means for providing an indifferent electrode remotely spaced from said patient's heart;

means for sensing the far-field ventricular electrogram from one electrode of said atrial electrode pair and said indifferent electrode;

means for sensing the far-field atrial electrogram from one electrode of ventricular electrode pair and said indifferent electrode; and means for examining the characteristics of the far-field atrial and ventricular electrograms of a series of one or more such electrograms to determine if they reflect a specific normal sinus tachycardia or a pathologic arrhythmia.

8. The apparatus of claim 7 further comprising:

means for digitizing the far-field electrograms and applying digitized signals to respective atrial and ventricular circulating buffers;

means for detecting the corresponding near-field atrial and ventricular electrogram and, after a preselected time delay, transferring the contents of the atrial and ventricular buffers into memory;

means for continuing to collect and transfer a predetermined number of atrial and ventricular far-field electrograms in memory; and means for comparing certain characteristics of the stored far-field electrograms with characteristics of reference rhythms and classifying the detected arrhythmia accordingly.

9. The apparatus of claim 8 further comprising:

means for prescribing predetermined therapy regimens for specific arrhythmias; and means for triggering the application of said predetermined therapies upon the determination that the far-field electrograms reflect corresponding predetermined pathologic arrhythmias.

10. The apparatus of claims 8 or 9 further comprising:

means for collecting far-field electrograms representing normal sinus and pathologic tachyarrhythmias from said patient's heart;

means for storing said normal sinus and pathologic far-field electrograms as a library of reference electrograms; and means for comparing said suspect far-field atrial and ventricular electrograms to said library of far-field atrial and ventricular reference electrograms to identify the most likely arrhythmia; and means for providing a therapy appropriate to the identified arrhythmia.

11. The apparatus of claim 7 further:

means for collecting far-field electrograms representing normal sinus and pathologic tachyarrhythmias from said patient's heart;

means for storing said normal sinus and pathologic far-field electrograms as a library of reference electrograms; and means for comparing said suspect far-field atrial and ventricular electrograms to said library of far-field atrial and ventricular reference electrograms to identify the most likely arrhythmia; and means for providing a therapy appropriate to the identified arrhythmia.

12. The apparatus of claims 7 or 11 further comprising:

means for prescribing predetermined therapy regimens for specific arrhythmias; and means for triggering the application of said predetermined therapies upon the determination that the far-field electrograms reflect predetermined pathologic arrhythmias.

13. An apparatus for preventing a pacemaker-mediated tachycardia from continuing in a dual chamber cardiac pacemaker having an atrial and ventricular pulse generator for providing synchronized atrial and ventricular stimulating pulses to electrodes situated in relation to the atrium and ventricle of the patient's heart comprising;

means for providing a close-spaced bipolar electrode pair in relation to said patient's atrium;

means for providing at least one ventricular electrode in relation to the patient's ventricle;

means for providing an indifferent electrode remote from the patient's heart;

means for coupling said bipolar electrode pair to a first sense amplifier and sensing the near-field atrial P-wave therefrom;

means for coupling said ventricular electrode and said indifferent electrode to a second sense amplifier for sensing the unipolar ventricular electrogram, including a far-field atrial P-wave electrogram component thereof;

means for measuring the intervals between successive bipolar atrial P-waves for deriving an atrial rate;

means for triggering the delivery of a ventricular stimulating pulse applied to said at least one ventricular electrode synchronously with the sensing of each of said bipolar atrial P-waves;

means for providing an upper rate limit;

means for comparing said atrial P-wave rate to said upper rate limit and in the event that said atrial rate exceeds said upper rate limit (1) sensing said far-field atrial P-wave electrogram; and (2) determining whether or not said far-field P-wave is sinus in origin or retrograde conducted from the ventricle; and means for taking corrective action to prevent pacemaker-mediated tachycardia in the event that said P-wave is retrograde in origin.

14. The apparatus of claim 13 further comprising:

means for digitizing the far-field electrograms and applying digitized signals to a circulating buffer;

means responsive to the detection of a suspect near-field atrial P-wave for transferring the contents of the far-field electrogram buffer into memory;

means for continuing to collect and transfer a predetermined number of suspect atrial far-field electrograms in memory; and means for comparing certain characteristics of the stored far-field electrograms with characteristics of reference rhythms and classifying the suspect atrial P-wave accordingly.

15. The apparatus of claim 14 further comprising:
means for collecting far-field electrograms representing normal sinus and pathologic (including retrograde conducted) P-waves from said patient's heart;

means for storing said normal sinus and pathologic far-field electrograms as a library of reference electrograms;

means for comparing said suspect far-field atrial and ventricular electrograms to said library of far-field atrial reference electrograms to identify the most likely match; and means for altering the function of the pacemaker to avoid tracking a pathologic atrial arrythmia or pacemaker-induced retrograde P-wave.

16. A method for preventing a pacemaker-mediated tachycardia from continuing in a dual chamber cardiac pacemaker having an atrial and ventricular pulse generator means for providing synchronized atrial and ventricular stimulating pulses to electrodes situated in relation to the atrium and ventricle of a patient's heart in the absence of spontaneous atrial and ventricular depolarizations recurring at a rate exceeding a lower pacing rate limit, comprising the steps of:

providing a close spaced bipolar electrode pair in relation to said patient's atrium;

providing at least one ventricular electrode in relation to the patient's ventricle;

providing an indifferent electrode remote from the patient's heart;

coupling said bipolar electrode pair to a first sense amplifier and sensing the near-field atrial P-wave therefrom;

coupling said ventricular electrode and said indifferent electrode to a second sense amplifier for sensing the unipolar ventricular electrogram, including the far-field atrial P-wave component thereof;

measuring the intervals between successive bipolar atrial P-waves for deriving an atrial rate;

triggering the delivery of a ventricular stimulating pulse applied to said at least one ventricular electrode synchronously with the sensing of each of said bipolar atrial P-waves;

providing an upper rate limit; and comparing said atrial P-wave rate to said upper rate limit and in the event that said atrial rate exceeds said upper rate limit: (1) sensing said far-field atrial P-wave electrogram; and (2) determining whether or not said far-field atrial P-wave is sinus in origin or retrograde conducted from the ventricle; and taking corrective action to prevent pacemaker mediated tachycardia in the event that said P-wave is retrograde in origin.

17. The method of claim 16 further comprising the steps of:

digitizing the far-field electrograms and applying digitized signals to a circulating buffer;

in response to the detection of a suspect near-field atrial P-wave transferring the contents of the far-field electrogram buffer into memory;

continuing to collect and transfer a predetermined number of suspect atrial far-field electrograms in memory; and comparing certain characteristics of the stored far-field electrograms with characteristics of reference rhythms and classifying the suspect atrial P-wave accordingly.

18. The method of claim 17 further comprising the steps of:

collecting far-field electrograms representing normal sinus and pathologic (including retrograde-conducted) P-waves from said patient's heart;

storing said normal sinus and pathologic far-field electrograms as a library of reference electrograms;

comparing said suspect far-field atrial and ventricular electrograms to said library of far-field atrial reference electrograms to identify the most likely match; and altering the function of the pacemaker to avoid tracking a pathologic atrial arrythmia or pacemaker induced P-wave.

19. In a dual chamber cardiac pacemaker system of the type having means for positioning at least one atrial electrode in relation to the atrium of a patient's heart; means for positioning at least one ventricular electrode in relation to the ventricle of a patient's heart; means for positioning a further indifferent electrode remote from the patient's heart; and pulse generator means adapted to be coupled to said atrial ventricular and indifferent electrodes for sensing atrial and ventricular electrical signals and providing pacing stimuli to said patient's heart for detecting pacemaker-mediated tachycardia further comprising:
  atrial sense amplifier means coupled to at least said atrial electrode and one other electrode for sensing electrical signals in the atrium;
  ventricular sense amplifier means coupled to at least said one ventricular electrode and a further electrode for sensing electrical signals in the ventricle;
  far-field sense amplifier means coupled to at least one ventricular electrode and said indifferent electrode for sensing far-field electrograms of the patient's heart;
  pulse generator means for providing a stimulating pulse to the ventricle at a first predetermined time after an electrical signal from the atrium is sensed, if no electrical signal from the ventricle is sensed within said first predetermined time;
  means for establishing an upper rate limit for the rate of recurrence of sensed electrical signals from the atrium;
  means for detecting whether said upper rate limit is exceeded by one or more sensed atrial electrical signals;
  means responsive to said detecting means and responsive to an atrial signal sensed by said atrial sense amplifier means for examining the far-field atrial electrical signal sensed by said far-field sense amplifier means coupled to said ventricular electrode and said indifferent electrode;
  means responsive to the examination of said far-field atrial electrical signal for determining whether or not said atrial electrical signal represents a normal behavior of the heart or a pathologic behavior of the heart including the or retrograde conduction of the immediately preceding ventricular depolarization.

20. The apparatus of claim 19 further comprising the steps of:
  digitizing the far-field electrograms and applying digitized signals to respective atrial and ventricular circulating buffers;
  detecting the corresponding near-field atrial and ventricular electrogram and, after a pre-selected time delay, transferring the contents of the atrial and ventricular buffers into memory;
  continuing to collect and transfer a predetermined number of atrial and ventricular far-field electrograms in memory; and
  comparing certain characteristics of the stored far-field electrograms with characteristics of reference rhythms and classifying the detected arrhythmia accordingly.

21. The apparatus of claim 20 further comprising the steps of:
  collecting far-field electrograms representing normal sinus and pathologic tachyarrhythmias from said patient's heart;
  storing said normal sinus and pathologic far-field electrograms as a library of reference electrograms; and
  comparing said suspect far-field atrial and ventricular electrograms to said library of far-field atrial and ventricular reference electrograms to identify the most likely arrhythmia; and
  providing a therapy appropriate to the identified arrhythmia.

22. In a dual chamber cardiac pacemaker system of the type comprising means for positioning at least one atrial electrode in relation to the atrium of a patient's heart; means for positioning at least one ventricular electrode in relation to the ventricle of a patient's heart; means for positioning a further indifferent electrode remote from the patient's heart; pulse generator means adapted to be coupled to said atrial ventricular and indifferent electrodes for sensing atrial and ventricular electrical signals and providing pacing stimuli to said patient's heart, the method for detecting pacemaker-mediated tachycardia comprising the steps of:
  sensing electrical signals in the atrium;
  sensing electrical signals in the ventricle;
  providing a stimulating pulse to the ventricle at a first predetermined time after an electrical signal from the atrium is sensed, if no electrical signal from the ventricle is sensed within said first predetermined time;
  establishing an upper rate limit for the rate of recurrence of sensed electrical signals from the atrium;
  detecting whether said upper rate limit is exceeded by one or more sensed atrial electrical signals, and, if so, examining the far-field atrial electrogram component of the electrical signal sensed between said ventricular electrode and said indifferent electrode; and
  in response to the examination of said far-field atrial electrogram, determining whether or not said atrial electrical signal represents a normal behavior of the heart or a pathologic behavior of the heart including retrograde conduction of the immediately preceding ventricular depolarization.

23. The method of claim 22 further comprising the steps of:
  digitizing the far-field electrograms and applying digitized signals to respective atrial and ventricular circulating buffers;
  detecting the corresponding near-field atrial and ventricular electrogram and, after a pre-selected time delay, transferring the contents of the atrial and ventricular buffers into memory;
  continuing to collect and transfer a predetermined number of atrial and ventricular far-field electrograms in memory; and
  comparing certain characteristics of the stored far-field electrograms with characteristics of reference rhythms and classifying the detected arrhythmia accordingly.

24. The method of claim 23 further comprising the steps of:
  collecting far-field electrograms representing normal sinus and pathologic tachyarrhythmias from said patient's heart;

storing said normal sinus and pathologic far-field electrograms as a library of reference electrograms; and comparing said suspect far-field atrial and ventricular electrograms to said library of far-field atrial and ventricular reference electrograms to identify the most likely arrhythmia; and providing a therapy appropriate to the identified arrhythmia.

25. A method for detecting a pacemaker mediated tachycardia in a dual chamber cardiac pacemaker of the type having a atrial and ventricular pulse generator means for providing synchronized atrial and ventricular stimulating pulses to electrodes situated in relation to the atrium and ventricular of a patient's heart in the absence of spontaneous atrial and ventricular depolarization occurring at a rate exceeding the lower pacing rate limit, comprising the steps of:

deriving a rate signal from successive spontaneous atrial depolarizations;

establishing a suspect upper rate limit for the synchronous tracking of spontaneous atrial depolarizations; and comparing said rate signal to said suspect upper rate limit and, in the event that said rate signal exceeds said suspect upper rate limit, examining the morphology of at least one electrogram of the spontaneous atrial depolarizations recurring at a rate exceeding said upper rate limit in order to determine whether or not said spontaneous atrial depolarizations are sinus in origin or pathologic, including those conducted from our preceding ventricular depolarization;

wherein said step of examining the morphology of at least one electrogram of the spontaneous atrial depolarizations in turn comprises the steps of:

sensing the far-field electrogram of the spontaneous atrial depolarization from at least one electrode disposed in the ventricle; and examining the characteristics of the far-field atrial electrogram of a series of one or more such electrograms to determine if the electrogram or electrograms reflect by it or their morphologic characteristics normal sinus rhythm at a rate exceeding the upper rate limit for a pathologic arrhythmia.

26. The method of claim 25 further comprising the steps of:

sampling and digitizing the far-field electrograms and applying digitized signals to an atrial circulating buffer;

detecting the corresponding near-field atrial and electrogram and, after a pre-selected time delay, transferring the contents of the atrial buffer into memory;

continuing to collect and transfer a predetermined number of atrial far-field electrograms in memory; and comparing certain characteristics of the stored far-field electrograms with characteristics of reference rhythms and classifying the detected arrhythmia accordingly.

27. The method of claim 26 further comprising the steps of:

collecting far-field electrograms representing normal sinus and pathologic tachyarrhythmias from said patient's heart;

storing said normal sinus and pathologic far-field electrograms as a library of reference electrograms; and comparing said suspect far-field atrial electrograms to said library of far-field atrial reference electrograms to identify sinus or the most likely arrhythmia; and providing a therapy appropriate to the identified arrhythmia.

28. An apparatus for detecting a pacemaker mediated tachycardia in a dual chamber cardiac pacemaker of the type having atrial and ventricular pulse generator means for providing synchronized atrial and ventricular stimulating pulses to electrodes situated in relation to the atrium and ventricle of a patient's heart in the absence of spontaneous atrial and ventricular depolarizations occurring at a rate exceeding the lower pacing rate comprising:

means for deriving a rate signal from successive spontaneous atrial depolarizations;

means for establishing a suspect rate for triggering of spontaneous atrial depolarizations; and means for comparing said rate signal to said suspect rate, and in the event said rate signal exceeds said suspect rate, examining the morphology of the electrogram of the spontaneous atrial depolarizations recurring exceeding said suspect rate in order to determine whether or not said spontaneous atrial depolarizations are sinus in origin or pathologic, including those retrograde conducted from a preceding ventricular depolarization;

wherein said means for comparing and examining in turn comprises:

means for sensing the far-field electrogram of the spontaneous atrial depolarization from at least one electrode deposed in the ventricle; and means for examining the characteristics of the far-field atrial electrogram of a series of one or more such electrograms to determine if the electrogram or electrograms reflect by it or their morphologic characteristics normal sinus rhythm or a pathologic arrhythmia.

29. The apparatus of claim 28 further comprising:

means for sampling and digitizing the far-field electrograms and applying digitized signals to an atrial and ventricular circulating buffer;

means for detecting the corresponding near-field atrial and electrogram and, after a pre-selected time delay, transferring the contents of the atrial buffer into memory;

means for continuing to collect and transfer a predetermined number of atrial far-field electrograms in memory; and means for comparing certain characteristics of the stored far-field electrograms with characteristics of reference rhythms and classifying the detected arrhythmia accordingly.

30. The apparatus of claim 29 further comprising:

means for collecting far-field electrograms representing normal sinus and pathologic tachyarrhythmias from said patient's heart;

means for storing said normal sinus and pathologic far-field electrograms as a library of reference electrograms; and means for comparing said suspect far-field atrial electrograms to said library of far-field atrial reference electrograms to identify sinus or the most likely arrhythmia; and means for providing a therapy appropriate to the identified arrhythmia.

31. A method for discriminating among various normal and pathologic arrhythmias of the human heart comprising the steps of:
  sensing the near-field electrograms from a first pair of electrodes situated in relation to one chamber of the patient's heart;
  determining the existence of a suspect rhythm from said near-field electrograms;
  sensing the far-field electrogram from at least one electrode situated in relation to another chamber of the patients' heart and a further electrode; and
  examining the characteristics of the far-field electrogram of a series of one or more such electrograms to determine if it or they reflect a specific normal sinus rhythm or a pathologic arrhythmia.

32. The method of claim 31 further comprising the steps of:
  digitizing the far-field electrograms and applying digitized signals to a circulating buffer;
  upon determining the existence of a suspect rhythm, detecting the corresponding near-field electrogram and transferring the contents of the buffer into memory;
  continuing to collect and transfer a predetermined number of digitized far-field electrograms in memory; and
  comparing certain characteristics of the stored far-field electrograms with characteristics of reference rhythms and classifying the detected arrhythmia accordingly.

33. The method of claim 32 further comprising the steps of:
  prescribing predetermined therapy regimens for specific arrhythmias; and
  triggering the application of said predetermined therapies upon the determination that the far-field electrograms reflect corresponding predetermined pathologic arrhythmias.

34. The method of claims 32 or 33 further comprising the steps of:
  collecting far-field electrograms representing normal sinus and pathologic tachyarrhythmias from said patient's heart;
  storing said normal sinus and pathologic far-field electrograms as a library of reference electrograms; and
  comparing said suspect far-field atrial and ventricular electrograms to said library of far-field atrial and ventricular reference electrograms to identify the most likely arrhythmia; and
  providing a therapy appropriate to the identified arrhythmia.

35. The method of claim 31 further comprising the steps of:
  collecting far-field electrograms representing normal sinus and pathologic tachyarrhythmias from said patient's heart;
  storing said normal sinus and pathologic far-field electrograms as a library of reference electrograms; and
  comparing said suspect far-field electrograms to said library of far-field atrial reference electrograms to identify the most likely arrhythmia; and
  providing a therapy appropriate to the identified arrhythmia.

36. The method of claims 31 or 35 further comprising the steps of:
  prescribing predetermined therapy regimens for specific arrhythmias; and
  triggering the application of said predetermined therapies upon the determination that the far-field electrograms reflect corresponding predetermined pathologic arrhythmias.

37. An apparatus for discriminating among various normal and pathologic arrhythmias of the human heart comprising:
  means for sensing the near-field electrograms from a first pair of electrodes situated in relation to one chamber of the patient's heart;
  means for determining the existence of a suspect rhythm from said near-field electrograms;
  means for sensing the far-field electrogram from at least one electrode situated in relation to another chamber of the patient's heart and a further electrode; and;
  means for examining the characteristics of the far-field electrogram of a series of one or more such electrograms to determine if it or they reflect a specific normal sinus rhythm or a pathologic arrhythmia.

38. The apparatus of claim 37 further comprising:
  means for digitizing the far-field electrograms and applying digitized signals to a circulating buffer;
  upon determining the existence of a suspect rhythm, means for detecting the corresponding near-field electrogram and transferring the contents of the buffer into memory;
  means for continuing to collect and transfer a predetermined number of digitized far-field electrograms in memory; and
  means for comparing certain characteristics of the stored far-field electrograms with characteristics of reference rhythms and classifying the detected arrhythmia accordingly.

39. The apparatus of claim, 38 further comprising:
  means for prescribing predetermined therapy regimens for specific arrhythmias; and
  means for triggering the application of said predetermined therapies upon the determination that the far-field electrograms reflect corresponding predetermined pathologic arrhythmias.

40. The apparatus of claims 37 or 38 further comprising:
  means for collecting far-field electrograms representing normal sinus and pathologic tachyarrhythmias from said patient's heart;
  means for storing said normal sinus and pathologic far-field electrograms as a library of reference electrograms; and
  means for comparing said suspect far-field atrial and ventricular electrograms to said library of far-field atrial and ventricular reference electrograms to identify the most likely arrhythmia; and
  means for providing a therapy appropriate to the identified arrhythmia.

41. The apparatus of claim 37 further:
  means for collecting far-field electrograms representing normal sinus and pathologic tachyarrhythmias from said patient's heart;
  means for storing said normal sinus and pathologic far-field electrograms as a library of reference electrograms; and means for comparing said suspect far-field electrograms to said library of far-field reference electrograms to identify the most likely arrhythmia; and
means for providing a therapy appropriate to the identified arrhythmia.

42. The apparatus of claims 37 or 41 further comprising:

means for prescribing predetermined therapy regimens for specific arrhythmias; and
means for triggering the application of said predetermined therapies upon the determination that the far-field electrograms reflect corresponding predetermined pathologic arrhythmias.

* * * * *